United States Patent [19]
Heilig et al.

[11] Patent Number: 5,939,275
[45] Date of Patent: *Aug. 17, 1999

[54] MESANGIAL CELL LINES AS MODELS FOR THE STUDY AND TREATMENT OF DIABETIC TISSUE COMPLICATIONS

[76] Inventors: Charles W. Heilig, 28 Whittler's Ridge, Pittsford, N.Y. 14534; Svend O. Freytag, 1778 Bournmouth, Grosse Point Woods, Mich. 48202; Bruce L. Riser, 409 Brewer St., Marshall, Mich. 49068

[*] Notice: This patent issued on a continued prosecution application filed under 37 CFR 1.53(d), and is subject to the twenty year patent term provisions of 35 U.S.C. 154(a)(2).

[21] Appl. No.: 08/522,571
[22] Filed: Sep. 1, 1995
[51] Int. Cl.$^6$ .................................................. G01N 33/567
[52] U.S. Cl. .................... 435/7.21; 435/7.92; 435/320.1; 435/353; 536/23.1
[58] Field of Search .............................. 435/240.2, 320.1, 435/4, 7.21, 7.92, 353; 536/23.1

[56] References Cited

PUBLICATIONS

Abboud, "Platelet–derived growth factor and mesangial cells" *Kidney Int.*, 41:581–583 (1992).
Abboud et al., "Production of platelet–derived growth factorlike protein by rat mesangial cells in culture" *J. Clin. Invest.*, 80:675–683 (1987).
Ayo et al., "High glucose causes an increase in extracellular matrix proteins in cultured mesangial cells" *Am. J. Pathol.*, 136:1339–1348 (1990).
Ayo et al., "Increased extracellular matrix synthesis and mRNA in mesangial cells grown in high glucose medium" *Am. J. Physiol.* 260 (Renal Fluid and Electrolyte Physiol. 29):F185–191 (1991a).
Ayo et al., "High glucose increases diacylglycerol mass and activates protein kinase C in mesangial cell cultures" *Am. J. Physiol.* 261 (Renal Fluid Electrolyte Physiol. 30):F571–F577 (1991b).
Baldwin, "Mammalian passive glucose transporters: members of a ubiquitous family of active and passive transport proteins" *Biochem. Biophys. Acta*, 1154:17–49 (1993).
Barbosa et al., "Effect of glycemic control on early diabetic renal lesions . . . " *J. Am. Med. Assoc.*, 272:600–606 (1994).
Bilous et al., "Mean glomerular volume and rate of development of diabetic nephrophathy" *Diabetes*, 38:1142–1147 (1989a).
Bilous et al., "The effects of pancreas transplantation on the glomerular structure of renal allografts . . . " *New Engl. J. Med.*, 321:80–85 (1989b).
Brosius et al., "Insulin–responsive glucose transporter expression in renal microvessels and glumeruli" *Kidney Int.*, 42:1086–1092 (1994).
Chatzilias and Whiteside, "Cellular mechanisms of glucose–induced myo–inositol transport upregulation . . . " *Am. J. Physiol.*, 267 (Renal Fluid Electrolyte Physiol)36:F459–F466 (1994).

Choi et al., "Rat mesangial cell hypertrophy in response to transforming growth factor–$\beta 1$" *Kidney Int.*, 44:948–958 (1993).
Cortes et al., "Effects of early diabetes on uridine diphosphosugar synthesis in the rat renal cortex" *Kidney Int.*, 21:676–682 (1982).
Craven and Derubertis, "Protein kinase C is activated in glomeruli from streptozotocin diabetic rats . . . " *J. Clin. Invest.*, 83:1667–1675 (1989).
Danne et al., "Effect of high glucose on type IV collagen production by cultured glomerular epithelial . . . " *Diabetes*, 42:170–177 (1993).
Diabetes Control and Complication Trial Research Group. "The effect of intensive treatment of diabetes . . . " *New England Journal of Medicine* 329(14):977–86 (Sep. 30, 1993).
Doi et al., "Modified colorimetric ninhydrin method for peptidase assay" *Anal. Biochem.*, 118:173–184 (1981).
Dumler and Cortes, "Uracil ribonucleotide metabolism in rat and human glomerular epithelial and mesangial cells" *Am. J. Physiol.*, 225(Cell Physiol 24):C712–C718 (1988).
Floege et al., "Infusion of platelet–derived growth factor or basic fibroblast growth factor induced selective glomerular . . . " *J. Clin. Invest.*, 92:2952–2962 (1993).
Freytag et al., "Ectopic expression of the CCAAT/enhancer–binding protein . . . " *Genes & Dev.*, 8:1654–1663 (1994).
Freytag and Geddes, "Reciprocal regulation of adipogenesis by Myc and C/EPA$\alpha$" *Science*, 256:379–382 (1992).
Fumo et al., "PKC and high glucose stimulate collagen $\alpha_1$ (IV) transcriptional activity . . . " *Am. J. Physiol.*, 267 (Renal Fluid Electrolyte Physiol. 36):F632–F638 (1994).
Gilbert et al., "Long–term glycemic control and the rate of progression of early diabetic kidney disease" *Kidney Int.*, 44:855–859 (1993).
Gilboa et al., "Transfer and expression of cloned genes using retroviral vectors" *BioTechniques*, 4(6):504–512, (1986).
Gould and Holman, "The glucose transporter family: structure, function and tissue specific expression" *Biochem. J.* 295:329–341 (1993).
Guzman and Crews, "Regulation of inositol transport by glucose and protein kinase C in mesangial cells" *Kidney Int.*, 42:33–40 (1992).

(List continued on next page.)

Primary Examiner—James Ketter
Assistant Examiner—Irem Yucel
Attorney, Agent, or Firm—Nixon, Hargrave, Devans & Doyle LLP

[57] ABSTRACT

An isolated and stable clone of mesangial cells which exhibit characteristics of diabetic cells when grown in normal glucose medium. The cells demonstrate an increase in glucose transport over normal mesangial cells and that provides a model for simulating diabetes in mesangial cells. Further, a stable, permanent clone of mesangial cells which underexpress GLUT1 mRNA and protein and which can be used therapeutically has been isolated.

9 Claims, 6 Drawing Sheets

OTHER PUBLICATIONS

Haneda et al., "Glucose enhances type IV collagen production in cultured rat glomerular mesangial cells" *Diabetologia*, 34:198–200 (1991).

Harrison et al., "Suppressed intrinsic catalytic activity of GLUT1 glucose transporters in insulin–sensitve 3T3–L1 adipocytes" *Proc. Natl. Acad. Sci. USA*, 88:7839–7843 (1991).

Harrison et al., "Insulin regulation of hexose transport in mouse 3T3–L1 cells expressing the human HepG2 glucose transporter" *J. Biol. Chem.*, 265:20106–20116 (1990).

Haverty et al., "Tubular antigen–binding proteins repress transcription of type IV collagen in the autoimmune . . ." *J. Clin. Invest.*, 89:517–523 (1992).

Heilig et al., "Identification of facilitative glucose transporters (GT) in mesangial cells (MC" *J. Am. Soc. Nephrol.*, 3:758 (Abstract) (1992).

Hiraki et al., "Growth factors rapidly induce expression of the glucose transporter gene" *J. Biol. Chem.*, 263:13655–13662 (1988).

Hundal et al., "Cellular mechanism of metrformin action involves glucose transporter translocation from an intracellular . . ." *Endocrinology*, 131:1165–1173 (1992).

Inman and Colowick, "Stimulation of glucose uptake by transforming growth factor β: . . ." *Proc. Natl. Acad. Sci. USA.*, 82:1346–1349 (1985).

Isaka et al., "Glomerulosclerosis induced by in vivo transfection transfection of transforming growth . . ." *J. Clin. Invest.*, 92:2597–2601 (1993).

Kaiser et al., "Differential regulation of glucose transport and transporters by glucose . . ." *Diabetes*, 42:80–89 (1993).

Kaname et al., "Autocrine secretion of transforming growth factor–β in cultured rat mesangial cells" *Kidney Int.*, 42:1319–1327 (1992).

Kitagawa et al., "Regulation of glucose transport activity and expression of glucose transporter mRNA . . ." *Biochem. Biophys. Acta*, 980:100–108 (1989).

Kitamura et al., "Gene transfer into the rat renal glomerlus via a mesangial cell vector: . . ." *J. Clin. Invest.*, 94(2):497–505 (1994).

Kreisberg et al., "High glucose elevates c–fos and c–jun transcripts and proteins in mesangial cell cultures" *Kidney Int.*, 46:105–112 (1994).

Kreisberg and Ayo, "The glomerular mesangium in diabetes mellitus" *Kidney Int.*, 43:109–113 (1993).

Kreisberg, "Hyperglycemia and microangiopathy. Direct regulation by glucose of microvascular cells" *Lab. Invest.*, 67:416–426 (1992).

Klip et al., "Regulation of expression of glucose transporters by glucose: a review . . ." *FASEB J.*, 8:43–53 (1994).

Ladson–Wofford et al., "High extracellular glucose concentrations increase receptors for transforming . . ." *J. Am. Soc. Nephrol.*, 5:696 (Abstract).

Larkin and Dunlop, "The link between hyperglycemia and diabetic nephropathy" *Diabtologia*, 35:499–504 (1992).

Okuda et al., "Elevated expression of transforming growth factor β and proteoglycan production . . ." *J. Clin. Invest.*, 86:453–462 (1990).

Marette et al., "Abundance, localization, and insulin–induced translocation of glucose transporters . . ." *Am. J. Physiol*, 236(Cell Physiol 32):C443–C452 (1992).

Mauer et al., "Structural–functional relationships in diabetic nephropathy" *J. Clin. Invest.*, 74:1143–1155 (1984).

McClain et al., *J. Biol. Chem.*, 262:14663–14671 (1987).

Merrall et al., "Insulin and platelet–derived growth factor acutely stimulate glucose transport . . ." *Biochem. Biophys. Acta*, 1177:191–198 (1993).

Mueckler et al., "Sequence and structure of a human glucose transporter" *Science*, 229:941–945 (1985).

Munro and Fleck, "The determination of nucleic acids" *Methods Biochem. Anal.*, 12:113–176 (1966).

Nahman et al., "Effects of high glucose on cellular proliferation and fibronectin production by cultured human mesangial cells" *Kidney Int.*, 41:396–402 (1992).

Olsen et al., "Collagen gene expression by cultured human skin fibroblasts" *J. Clin. Invest.*, 83:791–795 (1989).

Petersen et al., "Effect of insulin therapy on established diabetic nephropathy in rats" *Diabetes*, 37:1346–1350 (1988).

Phan et al., "Rat lung fibroblast collagen metabolism in bleomycin–induced pulmonary fibrosis" *J. Clin. Invest.*, 76:241–247 (1985).

Rasch, "Prevention of diabetic glomerulopathy in streptozotocin diabetic rats by insulin treatment. The mesangial regions" *Diabetologia*, 17:243–248 (1979).

Riser et al., "Intraglomerular pressure and mesangial stretching stimulate extracellular matrix . . ." *J. Clin. Invest.*, 90:1932–1943 (1992).

Riser et al., "Interactive effect of high glucose and stretch on mesangial cell (MC) collagen (COL) . . ." *Annual Meeting American Society of Nephology*, (submitted, 1995). [n/a—will send].

Rollins et al., "Platelet–derived growth factor regulates glucose transporter expression" *J. Biol. Chem.*, 236:16523–16526 (1988).

Sarabia et al., "Glucose transport in human skeletal muscle cells in culture. Stimulation by insulan and metformin" *J. Clin. Invest.*, 90:1386–1395 (1992).

Scheinman et al., "Collagen synthesis by human glomerular cells in culture" *Biochem. Biophys. Acta.*, 542:128–136 (1978).

Seyer–Hansen et al., "Renal hypertrophy in experimental diabetes. A morphometric study" *Diabetologia*, 18:501–505 (1980).

Shetty et al., "Induction of GLUT1 mRNA in response to inhibition of oxidative phosphorylation" *Am. J. Physiol.* 265 (Cell Physiol. 34):C1224–C1229 (1993).

Sivitz et al., "Regulation of glucose transporter messenger mRNA in insulin–deficient states" *Nature*, 340:72–74 (1989).

Steffes et al., "Amelioration of mesangial volume and surface alterations following islet transplantation in diabetic rats" *Diabetes*, 29:509–515 (1980).

Steffes et al., "Cell and matrix components of the glomerular mesangium in type I diabetes" *Diabetes*, 41:679–684 (1992).

Studer et al., "Role for protein kinase C in the mediation of increased fibronectin accumulation by mesangial . . ." *Diabetes*, 42:118–126 (1993).

Thorens et al., "Molecular physiology of glucose transporters" *Diabetes Care*, 13:209–218 (1990).

Tordjman et al., Differential regulation of two distinct glucose transporters species expressed in 3T3–L1 adipocytes . . . *Proc. Natl. Acad. Sci. USA*, 86:7761–7765 (1989).

Tsanev and Markov, "Substances interfering with spectrophotometric estimation of nucleic acids and their elimination . . ." *Biochem. Biophys. Acta.*, 42:442–452 (1960).

Varani et al., "Mesangial cell killing by leukocytes: role of leukocyte oxidants and proteolytic enzymes" *Kidney Int.*, 42:1169–1177 (1992).

Wang et al., "Coordinate regulation of glucose transporter function, number, and gene expression . . . " *J. Clin. Invest.*, 84:62–67 (1989).

Wolf et al., "High glucose–induced proliferation in mesangial cells is reversed by TGFβ" *Kidney Int.*, 42:647–656 (1992).

Yaoita et al., "Isolation and characterization of proteoglycans synthetized by cultured mesangial cells" *J. Biol. Chem.*, 265:522–531 (1990).

Ziyadeh et al., "Stimulation of collagen gene expression and protein synthesis in murine mesangial cells . . . " *J. Clin. Invest.*, 93:536–542 (1994).

Kitamura, et al. 1994, J. Clin. Invest. vol. 94 : pp. 497–505.

Kreisborg, et al 1983. Prostaglandins Leukotrienes and Medizine vol. 11 No. 4 pp. 431–442 (abstract only).

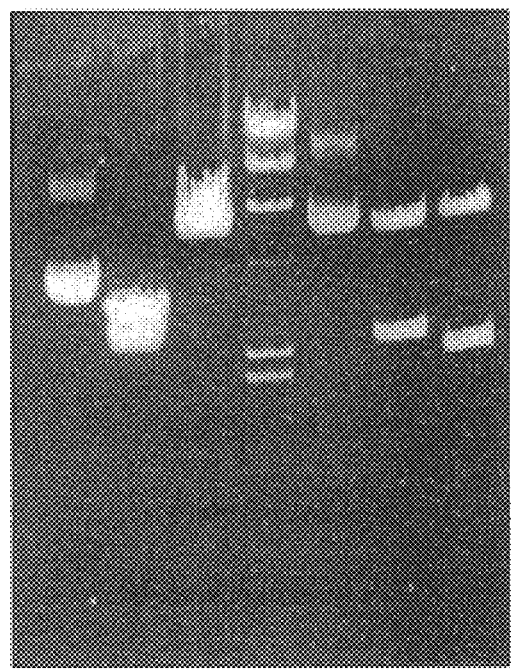
FIG. 5
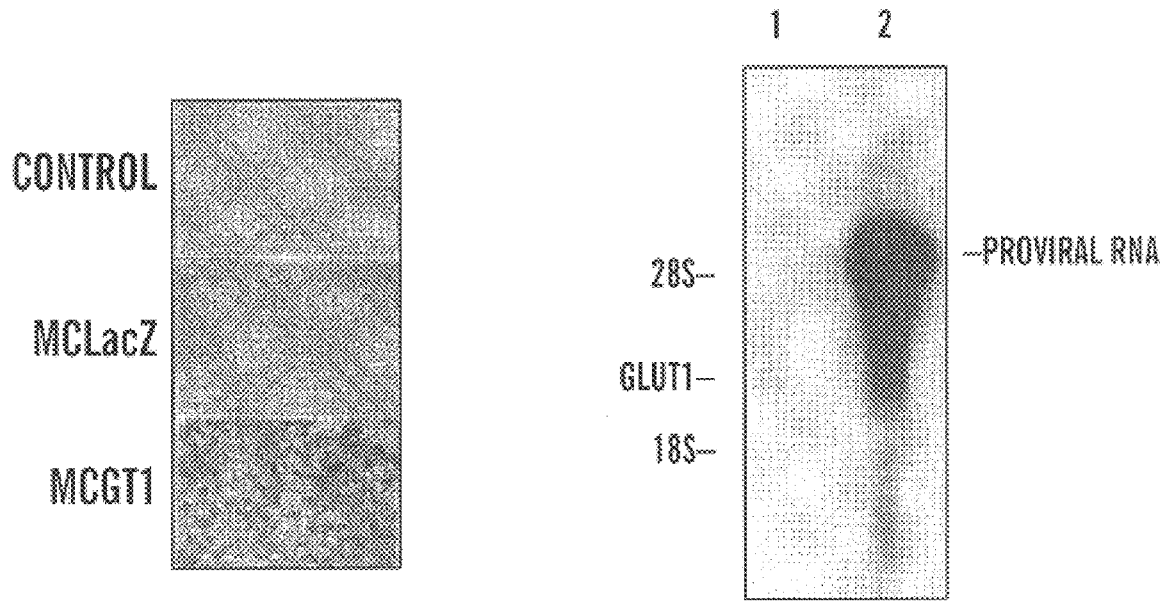
FIG. 6
FIG. 7

MESANGIAL CELL LINES AS MODELS FOR THE STUDY AND TREATMENT OF DIABETIC TISSUE COMPLICATIONS

GRANT REFERENCE

Research in this application was supported in part by grants from the National Institutes of Health, K08 DK01953 (Heilig), CA64295 (Freytag) and a grant from the Juvenile Diabetes Foundation International, 1921461 (Riser). The Government and the Juvenile Diabetes Foundation International have certain rights in the invention.

BACKGROUND OF THE INVENTION

1. Technical Field

The present invention relates to a model system for simulating diabetes. More specifically, the present invention relates to an isolated and stable clone of cells which exhibit characteristics of diabetic cells for use in testing antidiabetic drugs, and the pathogenesis of diabetic nephropathy. Further, the present invention relates to the use of a stable, permanent clone of mesangial cells which underexpresses GLUT1 mRNA and protein and which can be used therapeutically.

2. Background Art

Diabetic nephropathy, neuropathy, and retinopathy are the three most common tissue complications of diabetes. Diabetic kidney disease leads to end stage renal disease (ESRD) in approximately one-third of all patients suffering from diabetes. It has recently been established that hyperglycemia per se plays a significant role in the development of diabetic glomerulopathy and renal failure, however, the mechanisms by which it exerts its damaging effects are unknown (Diabetes Control and Complications Trial Research Group, 1993). Therefore, significant research efforts have been directed toward in vitro and in vivo investigation of the aforementioned mechanisms in order to discover the pathogenesis of diabetic nephropathy to develop therapies which may prevent or delay the complications of this disorder.

However, while researchers have attempted to develop therapies which might delay or prevent diabetic nephropathy, such as aldose reductase inhibitors and ACEIs (angiotensin converting enzyme inhibitors), no treatment to date has been optimal or highly effective in preventing the disease. Tight control of blood glucose levels puts patients at significant risk for hypoglycemia-induced symptoms or death. Therefore, new and more effective therapies are needed, based upon a better understanding of the disease mechanisms mediating diabetic nephropathy.

The central tenet of current theories addressing the mechanisms of development of diabetic nephropathy involves mesangial cell expansion and glomerular scarring due to increased production of extracellular matrix (ECM) components by mesangial cells (MCS). This has been proposed to be caused by several different mechanisms, however most of them either require or are facilitated by enhanced glucose uptake and metabolism. For instance, high extracellular glucose concentrations stimulate excessive ECM (scar tissue) production (Ayo et al., 1990; Ayo et al., 1991). The mechanisms by which this process is mediated are not clear, however enhanced mesangial cell aldose reductase (AR) activity with increased production of sorbitol, oxygen radicals, and vasodilator prostaglandins have been implicated, as have glycosylation of proteins, PKC (protein kinase C) activation, and TGF$\beta_1$ stimulation.

The renal glomerular lesion of human and experimental diabetes mellitus is characterized by glomerular hypertrophy (Bilous et al., 1989a; Seyer-Hansen et al., 1980) and the deposition of extracellular matrix in the form of diffuse thickening of the peripheral basement membrane and mesangial expansion (Mauer et al., 1984). The progressive accumulation of matrix in the mesangial areas, and the associated encroachment on neighboring capillaries with loss of filtration surface area, is considered as the main structural lesion responsible for the relentless decline in glomerular function (Mauer et al., 1984; Steffes et al., 1992). There is persuasive evidence that this critical change may be the result of an altered mesangial cell (MC) metabolism involving the extracellular matrix. MCs in tissue culture synthesize proteoglycans, fibronectin, laminin, thrombospondin and various forms of collagens, primarily type IV and type I (Yaoita et al., 1990; Scheinman et al., 1978; Ayo et al., 1990). Therefore, a metabolic derangement of these cells in diabetes resulting in the excessive formation and deposition of these matrix components is a likely determinant of mesangial expansion and glomerulosclerosis.

The knowledge on how extracellular matrix synthesis is controlled in MCs is only fragmentary. It is known that the synthetic activity may be stimulated by very diverse factors, notably the mechanical strain induced by distending forces during glomerular hypertension (Riser et al., 1992) and the action of TGF-$\beta$1 (Okuda et al., 1990). In diabetes, an obvious injurious alteration could be the continued presence of an abnormally high concentration of extracellular glucose. Recent evidence in humans (Bilous et al., 1989b; Barbosa et al., 1994) has confirmed early findings in animal studies (Rash, 1979; Steffes et al., 1980; Petersen et al., 1988) indicating that strict control of glycemia with insulin administration or successful pancreas transplantation may delay the onset and slow the progression of the characteristic mesangial matrix expansion. In addition, it has been amply demonstrated that MCs in tissue culture increase the production of fibronectin, laminin, collagen type IV as well as mRNA levels for these matrix proteins when incubated in the presence of elevated concentrations of glucose (Ayo et al., 1990; Ayo et al., 1991; Danne et al., 1993; Haneda et al., 1991; Nahman et al., 1992). Present indications are that even the effects of TGF-$\beta$ and mechanical strain are modulated by the level of extracellular glucose. (Riser, et al., 1995) Although it has been suggested that the increase in matrix synthesis may be partially due to the osmolar effect caused by high glucose concentrations (Nahman et al., 1992), most of the evidence accumulated thus far indicates that the change is related to the metabolism of glucose (Danne et al., 1993; Studer et al., 1993; Fumo et al., 1994). Glucose enters MCs by a facilitated diffusion process which is independent of insulin action (Kreisberg and Ayo, 1993). It has, therefore, been proposed that intracellular concentrations of glucose may approach those in the extracellular environment in diabetes (Kreisberg and Ayo, 1993). High intracellular concentrations of glucose may then increase extracellular matrix formation by activating the polyol pathway, inducing myoinositol depletion, increasing non-enzymatic glycosylation of proteins, or by generation of the second messengers inositol triphosphate and diacylglycerol followed by transcriptional activation of extracellular matrix genes (Fumo et al., 1994; Kreisberg, 1992).

Interrelating the above, diabetes is a complex disorder associated with the aforementioned hyperglycemia, altered expression of growth factors, signal transducers, cytokines, and hypertension with mesangial cell stretch.

Recent work by several investigators has provided strong evidence of a role, still undefined, for hyperglycemia per se in the development of diabetic tissue complications (Ayo et al., 1990; Ayo et al., 1991). This is further supported by the results from the DCCT trial (Diabetes Control and Complications Trial Research Group, 1993) which demonstrated that strict control of blood glucose levels in diabetic patients led to slowing of the development of renal, nerve, and other diabetic tissue complications which commonly develop. It must be concluded that there is considerable evidence demonstrating several mechanisms by which high extracellular glucose concentrations play a key role in the development of diabetic tissue complications.

It is presently not known whether glucose acts at the cell membrane to elicit the effects described above or whether it must be taken up by the cell. Because glucose is a substrate for sorbitol synthesis and because high extracellular glucose stimulates sorbitol and extracellular matrix production by mesangial cells, it is desirable to develop a model which would allow the investigation of the role of glucose uptake and transport separate from the extracellular effects of high glucose, such as osmolality, glycosylation of proteins, stimulation of phospholipase-C, as well as other effects (Larkin and Dunlop, 1992). Additionally, it is desirable to develop new drugs and test existing drugs that are potentially useful in the treatment of diabetes, and specifically, the treatment of diabetic nephropathy, by the use of such a cell line. Finally, it would be useful to develop such a cell line to facilitate the study of the pathogenesis, progression, prevention and therapy of diabetic nephropathy. Current therapies for the treatment of diabetic complications are suboptimal. Even patients who have relatively well regulated blood glucose levels may still be at risk for diabetic nephropathy, and other tissue complications.

SUMMARY OF THE INVENTION AND ADVANTAGES

The present invention provides a new in vitro model system for simulating diabetes in the mesangial cell (MC) and a gene therapy for diabetic tissue complications. More specifically, the present invention provides an isolated and stable clone of mesangial cells (MCS) which exhibit characteristics of diabetic cells and overexpress GLUT1. The present invention further provides a stable, permanent clone of mesangial cells which underexpress GLUT1 mRNA and protein and which can be used therapeutically.

In accordance with the present invention, three stable, cloned mesangial cell lines have been developed: mesangial cell clones engineered to express the reporter gene for β-galactosidase (control cell line) at high levels, to overexpress GLUT1, or to underexpress GLUT1. In addition, an effective new antisense GLUT1 DNA construct which downregulates GLUT1 in target cells, protecting them from the adverse effects of diabetes has been developed.

Overexpression of GLUT1 in mesangial cells, as for example the MCGT1 clone, reproduces the diabetic phenotype in these cells, without any increase in extracellular glucose concentration. The MCGT1 cells behave like diabetic cells, even in the absence of elevated extracellular glucose concentrations. The overexpressing GLUT1 cell line, along with the control MCLacZ cell line, are used for testing the effectiveness of new drugs expected to have therapeutic benefit for the kidney in diabetes and also to identify drugs that could have a harmful effect on the kidney in diabetes. These stably transduced cell lines will also be useful for studying the pathogenesis of diabetic kidney disease as it relates to excess glucose assimilation by the mesangial cell.

Underexpression of GLUT1 in mesangial cells, as for example the MCGT1AS clone, protects them from the harmful effects of high glucose in the diabetic range. Applicants have therefore developed an antisense-GLUT1 DNA expression construct for this purpose, called pWZLneoGLUT1AS, which can be transferred to mouse, rat, or human cells via the MoMuLV retrovirus. The MCGT1AS cells produced by transduction with the pWZLneoGLUT1AS expression construct, are shown to be protected from the adverse effects of high extracellular glucose concentrations.

In addition, DNA constructs developed to transduce mesangial cells, can also be used to transduce other cells in vitro or in vivo, whether via a viral vector or with modifications by other means, for therapeutic or nontherapeutic purposes.

BRIEF DESCRIPTION OF THE DRAWINGS

Other advantages of the present invention will be readily appreciated as the same becomes better understood by reference to the following detailed description when considered in connection with the accompanying drawings wherein:

FIG. 5 is a photograph of an ethium bromide stained gel demonstrating the pWZLneo GLUT1S DNA construct with the expected band patterns for a sense insertion of the human GLUT1 cDNA BamH1 fragment wherein Lane 1 is the uncut donor vector pSPGT, in Lane 2, this vector has been cut with BamH1 to remove the 2.6 Kb GLUT1 cDNA insert, in Lane 3, EcoR1 digestion linearizes the vector, Lane 4 contains the λHind III size markers, Lane 5 demonstrates the final uncut product pWZLneoGLUT1 resulting from splicing of the GLUT1 cDNA into the BamH1 cloning site of pWZLneo, Lane 6 demonstrates the product of a BamH1 digest of pWZLneoGLUT1 to confirm the presence of the 2.6 kb GLUT1 insert, the 5'→3' orientation of GLUT1 inside the pWZLneo vector is confirmed in lane 7, where digestion with EcoR1 results in the expected 6.0 Kb and 2.2 Kb bands.;

FIG. 6 is a photograph of immunogold-silver labeling of GLUT1 in mesangial cells, Top panel: normal mesangial cells exposed to nonimmune serum, middle panel: MCLacZ control cells exposed to GLUT1 specific antibody, bottom panel: MCGT1 cells exposed to GLUT1 specific antibody, the level of GLUT1 expression is demonstrated according to the intensity of the brown silver staining, original magnification was 40×;

FIG. 7 is a photograph of a Northern blot of GLUT1 in MCLacZ and MCGT1 cells, cells were chronically adapted to 8 mM glucose medium, and grown to confluence in this medium, total RNA was harvested for Northern analysis and a GLUT1 cDNA probe used to identify GLUT1 mRNAs in the two cell types, Lane 1 shows the endogenous 2.8 Kb mRNA of GLUT1 in the MCLacZ control cells, Lane 2 shows the new 5.6 Kb mRNA from the transduced GLUT1 sequence (sense) which was expressed at a level 18× control, so high that the signal obscured the endogenous GLUT1 mRNA at 2.8 Kb;

DETAILED DESCRIPTION OF THE INVENTION

Figure 1:
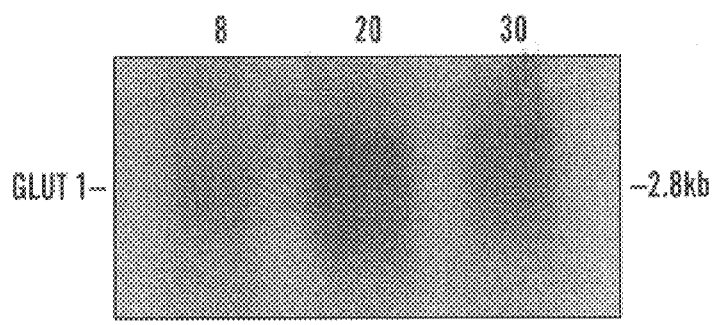
FIG. 1 is a photograph of a Northern blot of GLUT1 in normal mesangial cells (MCs), cells maintained in 8 mM glucose RPMI 1640 medium were seeded, grown for three days and culture plates were then split into three groups receiving 8, 20 or 30 mM glucose RPMI 1640 medium over the next three days, total RNA was then harvested and 20 µg loaded to each lane of sodium phosphate gels for electrophoresis, Northern blots were probed with a $^{32}$P-labeled GLUT1 cDNA probe.

The present invention provides an isolated and stable clone of mesangial cells which exhibit characteristics of diabetic cells and therefore can be used as a model system of diabetic nephropathy. The mesangial cells of the clone exhibit characteristics of diabetic cells without an increase in extracellular glucose. The cells demonstrate an increase in glucose transport over normal mesangial cells as demonstrated in the experimental section below. That is, the experimental section includes a control cell line that was transduced with a control gene, and still demonstrates normal glucose transport. The cells of the present invention show a significant increase over the normal amount of the control cells. Thus, the present invention provides stabilized, transduced, permanent cell lines exhibiting the characteristics of diabetic cells without an increase in extracellular glucose to demonstrate that an increase in glucose transport alone is a potent stimulus for the pathogenic characteristics of the cells.

Specifically, the cells have been engineered to overexpress GLUT1 mRNA and protein. GLUT1 is a facilitative transporter involved in the energy-independent uptake of glucose and is one of a group of integral membrane proteins, GLUT1- GLUT5 and GLUT7, which are encoded by separate genes. These proteins transport glucose with different efficiencies and kinetics (Baldwin, 1993).

By stating that the cells of a clone exhibit characteristics of diabetic cells, such characteristics are the production of:
  a) Excess mRNA for the extracellular matrix (ECM) proteins, fibronectin (FN), Collagen type I (Col.1), and Collagen type IV (Col.IV);
  b) Two to four times the normal amounts of ECM proteins;
  c) At least two times the normal amount of sorbitol;
  d) At least two times the normal amount of inositol.; and
  e) 2.5 times the normal amount of lactate.

A clone constructed in accordance with the present invention exhibits diabetic cell characteristics as listed above independent of increased extracellular glucose.

These characteristics are critical in view of the above-discussed effects of glucose on the normal cell membrane of mesangial cells. As stated above, glucose is a substrate for sorbitol synthesis and high extracellular glucose stimulates mesangial cell sorbitol and extracellular matrix production. Hence, the presently developed model system made in accordance with the present invention allows the investigation of the role of glucose uptake or transport separate from the extracellular effects of high glucose, such as osmolality, glycosylation of proteins, stimulation of phospholipase-C, as well as other extracellular effects.

As an example of the present invention, a clone designated MCGT1 (Deposited in the American Type Culture collection, 10801 University Boulevard, Manassas, Va. 20110-2209 under Accession Number CRL-12473 on Feb. 13, 1998), was engineered from normal mesangial cells which were transduced with a retrovirus carrying the sense GLUT1 DNA expression construct pWZLneoGLUT1. The latter was assembled from the Ariad Co. pWZLneo vector and a BamH1 full length GLUT1 cDNA obtained from Dr. Michael Mueckler, Washington University, St. Louis, Mo. The clone overexpresses Glut1 mRNA and protein.

This excess production of solutes by MCGT1 cells occurs in 8 mM (140 mg/dl) normal glucose medium. That is, there is no increase in extracellular glucose concentration (eg. 20 mM or 30 mM glucose) to explain the overproduction of these substances as observed in diabetes. Hence, the MCGT1 clone constructed in accordance with the present invention exhibits diabetic cell characteristics independent of increased extracellular glucose concentrations. These characteristics are critical in view of the above-discussed effects of glucose on the normal cell membrane of mesangial cells. As stated above, glucose is a substrate for sorbitol synthesis and high extracellular glucose concentration stimulates mesangial sorbitol and extracellular matrix production. Hence, the presently developed model system made in accordance with the present invention allows for investigation of the role of glucose uptake or transport separate from the extracellular effects of high glucose, such as hyperosmolality, glycosylation of proteins, stimulation of phospholipase-C, hyperosmotic stimulation of aldose reductase to produce sorbitol, etc., as well as other foreseen and unforseen extracellular effects.

The present invention further provides a control clone (cell line), MCLacZ (Deposited in the American Type Culture Collection, 10801 University Boulevard, Manassas, Va. 20110-2209 under Accession Number CRL-12475 on Feb. 13, 1998), showing what would be considered a control or relatively "normal amount" of glucose transport.

The present invention further includes stable, permanent clones of mesangial cells which underexpress GLUT1 mRNA and protein, demonstrate reduced glucose uptake, and demonstrate 3-fold lower FN gene expression compared to MCLacZ control cells under 20 mM high glucose conditions simulating diabetes.

Recombinant methods known in the art can be used to achieve the sense, antisense or triplex inhibition of a target nucleic acid. For example, vectors containing antisense nucleic acids can be employed to express protein or antisense message to reduce the expression of the target nucleic acid and therefore its activity. Using such methodology a clone designated MCGT1AS (Deposited in the American Type Culture Collection, 10801 University Boulevard, Manassas, Va. 20110-2209 under Accession Number CRL-12474 on Feb. 13, 1998) was engineered using an antisense construct as described herein below in the Example section.

The present invention further provides a method of using the antisense GLUT1 transduced cells. Mesangial cells can be protected from the deleterious effects of high glucose concentrations by the transduction or transfection of mesangial cells in vivo, thereby protecting the kidney, from hyperglycemia in diabetes as is known in the art. In addition, the transduced cells themselves may be used to replace endogenous mesangial cells in vivo, by mesangial cell transfer (transplant) as is known in the art (Kitamura et al., 1994). This method involves the replacement of mesangial cells of a living organism by mesangial cells from a cell line engineered as in the present invention to underexpress GLUT1. The mesangial cells can be removed from a patient and treated by the method of the present invention such that they underexpress GLUT1 and then returned to the patient. These modified mesangial cells, protected from hyperglycemia by their reduced glucose transport capacity, would protect the renal glomeruli from diabetic glomerulosclerosis mediated by fibronectin (FN) and other ECM molecules which would otherwise be produced in excess in response to hyperglycemia.

The present invention provides as an example three, stable, transduced clones of mesangial cells (MCLacZ, MCGT1, MCGT1AS) which are permanent cells lines unchanged with passage. The MCLacZ cells are the control line. MCGT1 cells overexpress GLUT1 and express characteristics of diabetic cells. These cells express these characteristics despite the absence of a high extracellular glucose concentration in the medium. Therefore, enhanced glucose transport alone was demonstrated to recreate the diabetic phenotype. Applicants have also demonstrated enhanced GLUT1 expression and glucose uptake in normal mesangial cells subjected to 20 mM high glucose medium for three or more days. MCGT1AS cells were designed to underexpress GLUT1, as a model for protection from the adverse effects of high glucose in diabetic concentrations (eg. 20 mM glucose=360 mg/dl).

The present invention provides a new mesangial cell line which overexpresses the GLUT1 glucose transporter thereby providing a convenient and effective model for the investigation of glucose transport-dependent pathways, a test system for demonstrating the effectiveness of antidiabetic therapies and post-therapies, and a facilitator for the study of diabetic nephropathy pathogenesis, progression, prevention and therapy. More specifically, the present invention can be used to test the effectiveness of antidiabetic drugs vis-a-vis their affect on inhibiting multiple glucose toxic pathways which are believed to contribute to diabetic glomerulosclerosis and kidney failure.

The central process in the development of diabetic nephropathy is excessive production of ECM (extracellular matrix) by mesangial cells, as exhibited by MCGT1 cells in 8 mM glucose RPMI 1640 medium. Therefore, in order to assess the kidney protective effect of a candidate drug, ECM production by MCGT1 cells (and MCLacZ control cells) is measured in the presence and absence of the drug in predetermined doses. An effective drug will partially or completely decrease ECM production of MCGT1 cells to the level of ECM production exhibited by MCLacZ control cells. ECM production—fibronectin (FN), laminin (LN), Collagen IV (ColIV) and collagen I (ColI) is measured by ELISA as described herein below or by equivalent methods.

The present invention further provides DNA constructs and an antisense DNA expression construct as described in the Example section hereinbelow and which were used in the development of the mesangial clones of the present invention.

The present invention further provides a useful tool for investigating the physiologic functions of GLUT1 as opposed to the functions of other GLUT isoforms found in other tissues which have different kinetics and patterns of expression.

Although the present invention utilizes a cell line grown in normal glucose medium and exhibits the disturbed metabolism characteristics of diabetic or high glucose-exposed mesangial cells in such normal glucose medium, such cells can also be studied under high glucose conditions if desired.

Also, the above test can be conducted utilizing the control mesangial cell line transduced with the LacZ gene developed as discussed above. This cell line controls for the cellular effects of the transduction process and provides a "normal" response for comparison.

Further, the present invention provides a useful antisense GLUT1 DNA construct having potential therapeutic effect for the treatment of complications of diabetes. The antisense DNA construct can be used to down regulate the endogenous GLUT1 glucose transporter of mesangial cells and thereby slow glucose uptake in the activity of downstream pathways which are overactive in diabetes, such as extracellular matrix production, aldose reductase activity with sorbitol production and increase NAD which oxidizes glutathione, oxygen radical formation from glucose itself, DAG formation from glycolytic intermediates and subsequent PKC activation which lead to increased extracellular matrix components formation and other effects. This is feasible, without loss of cell viability, because most cells normally express more glucose transporters in the plasma membrane than are needed for normal metabolism. That is, such cells have an excess of transporters.

The constructs can be delivered either in vivo or to a patient's cells being cultured in vitro utilizing vectors, for example. The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1994), Chang et al., *Somatic Gene Therapy*, CRC Press, Ann Arbor, Mich. (1995), Vega et al., *Gene Targeting*, CRC Press, Ann Arbor, Mich. (1995) and Gilboa, et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

An example of a DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The studies set forth in the experimental section herein below were initiated based on applicants' hypothesis that the glucose-induced stimulation of extracellular matrix formation by MCs may not necessarily require the presence of supraphysiological concentrations of glucose if there is an increased transport and thus, excessive bioavailability of this hexose as substrate for metabolism. Except for unique tissues in which glucose is concentrated by an active process involving $Na^+$/glucose cotransporters, i.e., renal proximal tubule and intestinal epithelial cells, glucose enters cells by the passive process of facilitated diffusion. In this process, specific integral membrane proteins, identified as the GLUT family, transport glucose down a concentration gradient. Preliminary work on the identification of glucose transporters in MCs suggests that GLUT1 may be the preponderant isoform (Kikkawa et al., 1992; Heilig et al., 1992). This transporter, considered to be responsible for constitutive glucose transport, is known to be regulatable in some tissues. It is also the most ubiquitously distributed of the GLUT isoforms in vivo, and is expressed in virtually all cultured cells (Klip et al., 1994). The high affinity of GLUT1 for glucose (Kahn, 1992; Baldwin, 1993) ensures that this transporter functions at, or close to, its $V_{max}$ under normal physiological and diabetic hyperglycemic conditions. In MCs, saturation of glucose uptake has been reported at the 30 to 35 mM level (Kreisberg and Ayo, 1993). Therefore, enhanced glucose uptake through GLUT1 may possibly be achieved by raising its extracellular concentration up to about 30 mM, by increasing the intrinsic activity of the transporter (Harrison et al., 1991), or through stimulation of GLUT1 expression and/or translocation from intracellular sites to the plasma membrane (Harrison et al., 1990). However, it has not been determined in MCs if enhanced GLUT1-mediated transport per se is associated with an increased utilization of substrate, i.e., whether transport activity may be an important modulator of glucose metabolism.

To test the hypothesis, the production of extracellular matrix in rat MCs exposed to high glucose concentrations was compared with that in the same cells exposed to physiological levels of extracellular glucose, but overexpressing GLUT1 protein. The results reported herein differentiate the effects of extracellular glucose concentration from those of enhanced intracellular glucose availability and utilization on extracellular matrix formation, providing new insights into the pathogenesis of the glomerular lesion of diabetes.

Figure 2:
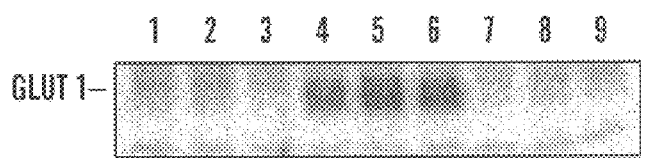
FIG. 2 is a photograph of an immunoblot of GLUT1 in normal mesangial cells, cells maintained in 8 mM glucose medium were seeded and grown for three days and culture plates were then split into three groups receiving 8 mM glucose medium, 20 mM glucose medium, or 8 mM glucose medium plus 12 mM mannitol (to equal the osmolality of the 20 mM glucose medium), total proteins were harvested for each group and 50 µg loaded to each lane of 10% SDS-PAGE gels, GLUT1 was labeled with specific Ab, at 48 kD.
Figure 3:
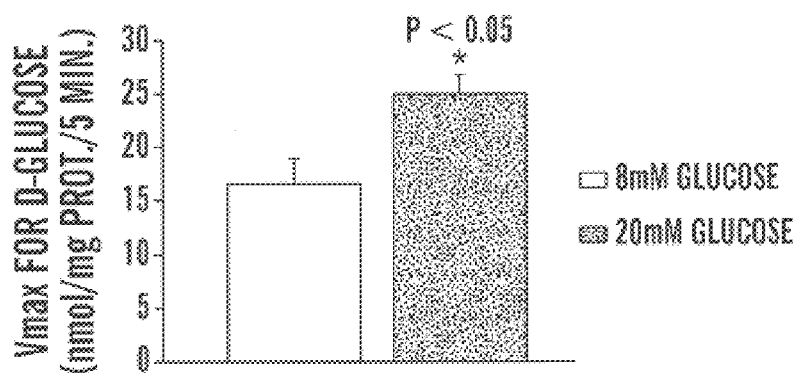
FIG. 3 is a bar graph of the maximum velocity ($V_{max}$) of glucose uptake in normal mesangial cells, MCs chronically adapted to 8 mM glucose RPMI medium were seeded and grown for 3 days in this medium and were then split into two groups, to receive either 8 or 20 mM glucose medium for the next three days, cells were then harvested and [$^3$H]2-deoxyglucose uptake measurements performed for determination of $V_{max}$ and $K_m$, measurements for Vmax (nmol glucose/mg protein/5 minutes) are shown (*P<0.05), the $K_m$ for GLUT1 is low enough that it is saturated even at physiologic glucose concentrations, and cells are operating at $V_{max}$.
Figure 4:
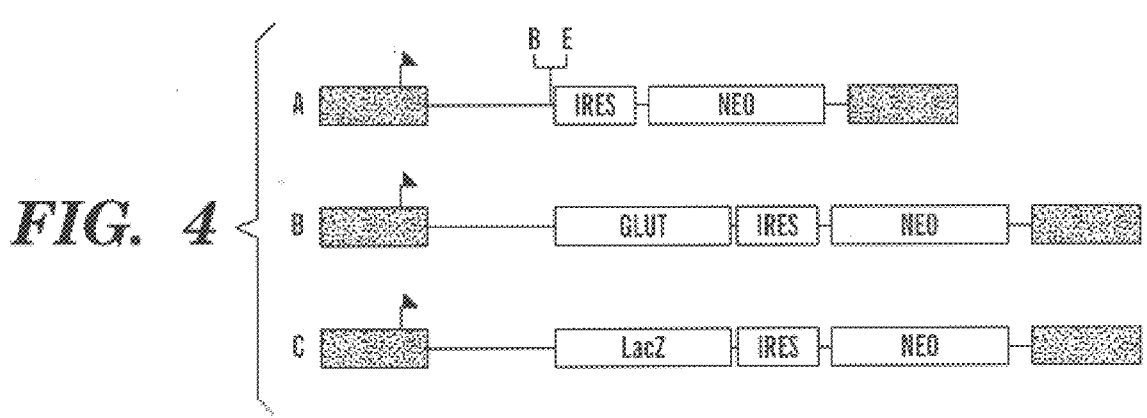
FIGS. 4A–C is a diagram of the pWZLneo-based retroviral expression vectors, (A) the pWZLneo vector contains an internal ribosomal entry site (IRES) from the encephalomyocarditis virus, it also contains the neo$^R$ gene (NEO) coding for resistance to G418, (B) the human GLUT1 cDNA is spliced into the BamH1 [B]/EcoR1 [E] multiple cloning region of the vector, (C) to produce a control vector, the bacterial LacZ cDNA (LacZ) was similarly spliced into pWZLneo in place of GLUT1, Arrows indicate the transcription initiation site.

Applicants recently identified GLUT1 protein as the predominant mesangial cell transporter. This transporter is saturated at physiologic glucose concentrations. Subsequently, the mechanism of enhanced glucose uptake under high glucose conditions was identified, as enhanced synthesis of GLUT1 protein (FIGS. 1, 2, 3). D-glucose was the specific effector, since mannitol at the same hyperosmolality had no effect on GLUT1 expression (FIG. 2). Therefore, high glucose in the diabetic range (20 mM glucose) stimulates increased glucose uptake by the mesangial cell (FIG. 3), which leads to excessive ECM production and glomerular scarring, causing destruction of glomeruli and loss of kidney function in diabetes.

In this work it was shown that MCs overutilizing glucose synthesize and accumulate increased amounts of extracellular matrix even in the absence of elevated extracellular glucose concentrations. Clearly, it can be concluded from this finding that changes directly related to the presence of a high glucose concentration, i.e. extracellular hyperosmolarity and abnormally increased transmembrane gradients of glucose, are not necessarily required for the excessive formation of extracellular matrix by MCs in a diabetic milieu. This study shows, instead, that the relevant factor is linked to metabolic changes occurring during the overutilization of glucose which follows its enhanced uptake.

MCGT1 cells of the present invention demonstrated a markedly increased transport of a glucose analog which was due to an increased $V_{max}$ while affinity of the transporter remained unchanged. The measured Km in MCGT1 cells and in their MCLacZ controls of 3.1–3.7 mM is consistent with the values of 1–7 mM determined by similar 2-deoxyglucose uptakes in multiple tissues for GLUT1 (Thorens et al., 1990; Gould and Holman, 1993). In conditions of 8 mM glucose concentration, this transporter is, thus, fully saturated and any increases in uptake would be the result of changes in activity translocations, or synthesis, of the transporter. This suggests that under conditions of high glucose concentrations exaggerated glucose uptake and increased extracellular matrix synthesis may be related to increased expression of functional GLUT1.

The increased glucose uptake in MCGT1 cells was also accompanied by a high net utilization of glucose and an exaggerated formation of lactic acid and sorbitol. In addition, it was also associated with the accumulation of myo-inositol. Therefore, alterations related to myo-inositol depletion may be excluded as causative factors for the glucose-stimulated extracellular matrix formation.

The facilitative transporters involved in the energy-independent uptake of glucose comprise a group of integral membrane proteins, GLUT1- GLUT5 and GLUT7, which are encoded by separate genes. These proteins transport glucose with different efficiencies and kinetics (Baldwin, 1993). GLUT6 is a pseudogene, GLUT7 functions in the endoplasmic reticulum membrane and GLUT5 is primarily an intestinal fructose transporter. The remaining GLUT isoforms, involved in the cellular transport of glucose, are expressed differently within tissues demonstrating distinct metabolism of this hexose, suggesting a close link between specific transporters and the handling of glucose through specific metabolic pathways (Kahn, 1992). The insulin-regulatable GLUT4 isoform has been identified in MCs (Brosius et al., 1994), however, its functional role remains in doubt since glucose transport and extracellular matrix synthesis in these cells do not appear to be influenced by insulin (Fumo et al., 1994; Kreisberg and Ayo, 1993).

As shown by the present invention it is possible to enhance glucose uptake by augmenting the transport capacity, resulting from increasing the number of transporters. To this end, the neo$^R$ gene encoding neomycin phosphotransferase and human GLUT1 or bacterial LacZ (as control) was transduced into a cloned line of rat MCs. The resultant MCGT1 cells demonstrated a marked increase in GLUT1 synthesis as shown by the overexpression of GLUT1 mRNA and GLUT1 protein. The overexpression of LacZ or GLUT1 in the G418-resistant surviving clones was generalized to all cells and well maintained after multiple passages in culture. In cells such as 3T3-L1 adipocytes in which GLUT1 intrinsic activity appears to be modulated, the heterologous expression of human GLUT1 is also subject to the same inhibitory control (Harrison et al., 1991). Therefore, it is expected that if the activity of the endogenous GLUT1 were regulated in MCs, the additional exogenous GLUT1 transporters expressed in the transduced cells of the present invention would be under the same form of control.

The effect of high glucose concentrations on MC growth in tissue culture has been variously reported as being neutral (Danne et al., 1993; Kreisberg and Ayo, 1993) or exerting inhibitory effects (Nahman et al., 1992; Moran et al., 1991). Applicants observed decreased proliferation and cell hypertrophy in cultures of normal MCs exposed to 35 mM glucose, according to the DNA and RNA/DNA values obtained at the end of the experimental period. Similar growth characteristics were demonstrated in a normal glucose environment by MCs overexpressing the GLUT1 transporter when compared to their LacZ-transduced controls. The mechanism by which this enhanced glucose uptake, whether elicited by increasing the extracellular concentration or by stimulating transport, may affect MC growth is not fully understood. However, it is likely that the process involves the induction of endogenous TGF-β1 expression and/or activation (Wolf et al., 1992). In long term cultures of MCs, high glucose concentrations stimulate TGF-β1 secretion and cause sustained inhibition of cell proliferation, cell hypertrophy and increased protein synthesis (Wolf et al., 1992; Choi et al., 1993). These changes are prevented by neutralizing antibody against TGF-β and they are not reproduced in an hyperosmolar environment obtained by the addition of L-glucose or mannitol (Wolf et al., 1992).

Applicants observed an increased cellular content of myo-inositol concomitant with the augmented glucose uptake and sorbitol accumulation in MCGT1 cells. This is an alteration similar to that seen in cells exposed to high glucose concentrations in which the $V_{max}$ of the Na$^+$-dependent myo-inositol cotransporter is increased (Guzman and Crews, 1992; Chatzilias and Whiteside, 1994). Although the precise mechanism for this effect has not been elucidated, it involves stimulation of the polyol pathway and activation of protein kinase C. These two metabolic alterations are likely to be present in the MCGT1 cells (see below).

As shown in previous studies (Ayo et al., 1990, Ayo et al., 1991; Danne et al., 1993; Haneda et al., 1991), high concentrations of extracellular glucose increased net formation of collagen in the medium and in the cell layer in MC cultures. In addition, as demonstrated by others (Ayo et al., 1990; Danne et al., 1993), an enhanced synthetic rate was identified as the major metabolic alteration responsible for the accumulation of collagen. Contrary to other studies (Ayo et al., 1991), however, the present invention shows associated changes in collagen catabolism and total protein synthesis. Collagen catabolism was accelerated by glucose, but this change was of insufficient magnitude to offset the markedly increased synthesis. In addition, protein secretion into the culture medium was also increased, although this change was of lesser magnitude than that for the accumulation of collagen. A possible cause for these discrepant results may be that, contrary to previous work, incorporation results in this study were corrected for changes in the specific activity of the amino acid precursor.

The collagen metabolic changes shown in MCGT1 cells incubated in normal glucose conditions qualitatively mirrored those observed in normal MCs exposed to high glucose concentration. However, when compared to their corresponding controls, MCGT1 cells exhibited a greater increase in total collagen synthesis (109% vs 69%) and in collagen accumulation (111–117% vs 81–90%) than normal MCs incubated in high glucose conditions. All four of the individual matrix components examined in the culture medium, collagen I, collagen IV, fibronectin and laminin, were increased 2.3 to 4.3-fold over values in MCLacZ cultures. In addition, the increased mRNAs for collagen I, collagen IV and fibronectin is consistent with the increased synthesis of these individual matrix components. Total protein secretion was also enhanced, although not to the same extent as for collagen accumulation. Therefore, in terms of growth characteristics, myo-inositol accumulation and collagen metabolism, MCs overexpressing the GLUT1 transporter in an 8 mM glucose environment behaved like normal MCs grown in 35 mM glucose.

Recent studies have begun to unravel the mechanisms by which an increased entry of glucose into MCs may stimulate extracellular matrix formation. MCs grown in a high ambient glucose concentration demonstrate activation of protein kinase C as a result of increased diacylglycerol mass (Kreisberg and Ayo, 1993; Ayo et al., 1991b). It has been proposed that protein kinase C modulates activator protein 1 complex (AP-1), the transcriptional product of jun and fos proto-oncogenes, which in turn, binds to specific sequences in the promoter regions of extracellular matrix genes (Kreisberg et al., 1994). This mechanism appears to be operative in vivo also, because diacylglycerol mass and protein kinase C activity are also increased in glomeruli from diabetic rats and in isolated normal glomeruli acutely exposed to high glucose concentrations (Craven and DeRubertis, 1989). Since the change in diacylglycerol formation is through an enhanced de novo synthesis from glycolytic intermediates (Studer et al., 1993; Kreisberg and Ayo, 1993; Ayo et al., 1991) in a process favored by the altered cellular redox state caused by the increased polyol pathway activity, it follows that the stimulation of extracellular matrix synthesis requires the accelerated metabolism of glucose.

Applicants' studies in transduced cells demonstrate that glucose transport is an important modulator in MCs for glucose utilization and for the glucose effects on extracellular matrix metabolism. In addition, the glucose-stimulated rate of extracellular matrix accumulation appears to depend to a greater degree on the capacity to transport glucose than on the actual extracellular concentration of the hexose. This underlines the potential importance of the regulation of GLUT1 expression and activity in MCs as a determinant of extracellular matrix deposition and mesangial expansion. Glucose flux via GLUT transporters may be regulated at the transcriptional level or by altering the rates of protein synthesis and degradation, changes in intrinsic activity, and the translocation of a vesicle-associated intracellular pool of transporters to the plasma membrane (Kahn, 1992). The latter, while being paramount in the GLUT4 activation by insulin, is of lesser importance for GLUT1-mediated transport due to the already preponderant localization of this isoform on the plasma membrane under basal conditions and its lesser translocation efficiency (Marette et al., 1992). A large variety of agents regulate GLUT1 expression (Baldwin, 1993). In endothelial cells and hepatocytes hypoxia and inhibition of oxidative phosphorylation induce GLUT1 expression (Shetty et al., 1993; Loike et al., 1992). The most commonly reported effects of glucose have been those caused by its deprivation in both insulin-responsive and insulin-nonresponsive cells. These consist of changes in the transport of the hexose in association with increased GLUT1 protein, with or without associated changes in GLUT1 mRNA (Klip et al., 1994). These effects are readily reversed by providing glucose. In contrast, in the adipose tissue and skeletal muscle of hyperglycemic animals with streptozotocin-induced diabetes, GLUT1 mRNA and GLUT1 protein are inappropriately unaffected (Klip et al., 1994; Sivitz et al., 1989).

The regulation of GLUT1 expression by growth factors is of particular importance as a potential element in the pathogenesis of diabetic mesangial expansion. PDGF and TGF-β are known to enhance glucose uptake, increase GLUT1 mRNA and promote GLUT1 expression in cultures of fibroblast cell lines (Inman and Colowick, 1985; Hiraki et al., 1988; Rollins et al., 1988; Kitagawa et al., 1989; Merrall et al., 1993). MCs, in turn, produce PDGF and TGF-β (Kitagawa et al., 1989; Merrall et al., 1993; Abboud et al., 1987; Kaname et al., 1992), thus having an autocrine system capable of regulating GLUT1 expression. This system may be activated in diabetes because high glucose concentrations increase the MC secretion of TGF-β and the expression of specific cellular receptors for this growth factor (Ladson-Wofford et al., 1994; Ziyadeh et al., 1994). Further, MCs respond to the same growth factors by increasing extracellular matrix formation in vitro (Ziyadeh et al., 1994; Abboud, 1992) and by inducing mesangial expansion and glomerulosclerosis in vivo (Floege et al., 1993; Isaka et al., 1993), but it is not known if GLUT1 overexpression participates in the mediation of this effect.

It is of interest that oral hypoglycemic agents, extensively used in the treatment of Type II diabetes, are highly effective in increasing GLUT1 expression and glucose transport. Metformin and the sulfonylureas tolbutamide and tolazamide increase GLUT1 protein, GLUT1 mRNA and the translocation of this transporter to the plasma membrane in L6 myotubes and 3T3-L1 adipocytes (Sarabia et al., 1992; Hundal et al., 1992; Tordjman et al., 1989; Wang et al., 1989). The relative effect of metformin is particularly intense in conditions of high glucose concentrations (Sarabia et al., 1992). The administration of these agents may result in the paradoxical circumstance in which an improvement in glycemia may be associated with greater glucose uptake and higher risk for the development of complications in GLUT1-expressing tissues. Therefore the present invention provides a means of identifying such drugs prior to use.

This work suggests that increased glucose uptake, rather than the level of glycemia per se, may be a major metabolic determinant in the development of mesangial expansion and glomerulosclerosis in diabetes. If MC GLUT1 expression and activity varies in human diabetes, this could explain the obscure predisposition of only a limited group of patients to the development of renal disease and the poor correlation between glycemic levels and progression of nephropathy in some of these cases, even after long periods of diabetes (Gilbert et al., 1993).

Figure 15:
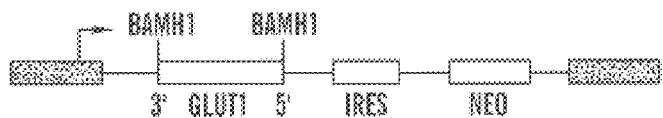
FIG. 15 is a map of PWZLneoGLUT1AS DNA expression construct, the pWZLneo vector was obtained from Ariad Co., Cambridge, Mass., a near full length human BamH1 GLUT1 cDNA fragment was spliced into the multiple cloning site of the vector in the antisense orientation, and confirmed by Southern analysis, this construct was then used to transfect the ΨCRE fibroblast packaging cell line, which produced live virus carrying the RNA message.

The invention further provides an antisense GLUT1 cDNA construct, pWZLneoGLUT1AS, as shown in FIG. 15 plus a stably transduced MC line, MCGT1AS which demonstrates downregulation of GLUT1 and glucose uptake. This construct was developed utilizing standard recombinant DNA technology to splice a full length human BamH1 GLUT1 cDNA fragment into the multiple cloning site of the pWZLneo vector in the 3' to 5' antisense orientation. This antisense construct can be used in vitro as well as in vivo to downregulate GLUT1 and glucose uptake, in mouse, rat, and human cells. A method is available by which mesangial cells in vivo can be induced to proliferate, thereby allowing them to take up retroviral-mediated gene constructs (Kitamura et al., 1994). Applicants have transferred constructs to mesangial cells in vitro via the MoMuLV retrovirus vector, pWZLneo. Similar DNA constructs can be transferred via other mechanisms, such as adenoviruses to nonreplicating cells, other viruses, or nonviral mechanisms (Bosh et al., 1993; Imai et al., 1994) and also as discussed herein above. As an example and as discussed herein, a mesangial cell line MCGT1AS was developed, in which glucose uptake was downregulated by antisense inhibition of GLUT1 using the present invention pWZLneoGLUT1AS DNA expression construct. The MCGT1AS cells themselves, or similarly transduced patient cells, can be transferred to glomeruli in vivo to replace endogenous mesangial cells via mesangial cell gene transfer (Kitamura et al., 1994; Isaka et al., 1993). The glomeruli containing the transplanted mesangial cells, replacing their original MCs, would then be protected from the adverse effects of hyperglycemia as observed in diabetes. This would potentially prevent diabetic nephropathy with renal failure. A similar antisense gene therapy may also be possible for protecting other non renal tissues from the complications of diabetes.

Figure 19:
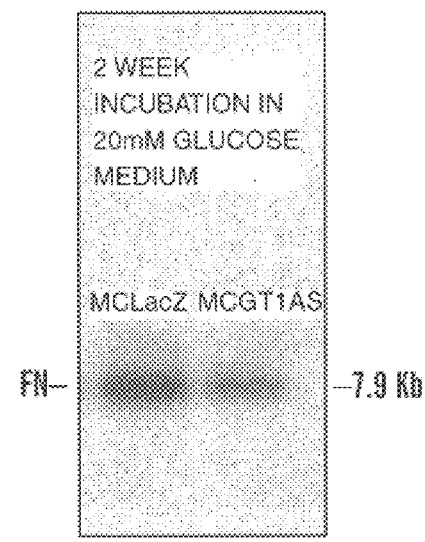
FIG. 19 is a photograph of protection of mesangial cells from high glucose by retroviral-mediated antisense inhibition of GLUT1, the effects of high (20 mM) extracellular glucose concentration on FN gene expression were determined in MCGT1AS vs. MCLacZ cells by Northern analysis, FN mRNA is normally increased in MCs by 20 mM high glucose, the MCGT1AS cells however had 3-fold less FN mRNA than control MCLacZ cells in 20 mM high glucose, indicating protection, presumably due to their low GLUT1 expression and low glucose uptakes.

This antisense GLUT1 construct may be used as an in vivo therapy to slow the development of diabetic nephropathy and other diabetic tissue complications. This is feasible because mammalian cells typically express more glucose transporters than are necessary to carry out normal metabolic processes. Applicants have found that downregulation of mesangial cell GLUT1 by antisense GLUT1 mRNA, can decrease glucose uptake, and thereby decrease expression of MC ECM genes such as FN in response to high glucose concentrations (20 mM) simulating diabetes (FIG. 19). In diabetes, FN deposits in excess in the mesangium, leading to kidney failure (Ayo et al., 1990; Ayo et al., 1991; Steffes et al., 1992). Further, based upon the observed regulation of sorbitol accumulation by GLUT1 expression, the MCGT1AS cells should accumulate less sorbitol in response to high extracellular glucose concentrations, again protecting the cell and the kidney from diabetes. Other pathways dependent on glucose which may contribute to diabetic nephropathy may also be downregulated in antisense GLUT1-treated cells, thereby protecting the cell (Larkin and Dunlop, 1992).

The methods used with and the utility of the present invention can be shown by the following non-limiting examples.

EXAMPLES

General methods in molecular biology

Standard molecular biology techniques known in the art and not specifically described were generally followed as in Sambrook et al., *Molecular Cloning: A Laboratory Manual*, Cold Springs Harbor Laboratory, New York (1992), and in Ausubel et al., *Current Protocols in Molecular Biology*, John Wiley and Sons, Baltimore, Md. (1994).

Materials

The purified extracellular matrix components utilized as standards included rat collagen type I (Upstate Biotechnology, Lake Placid, N.Y.), murine collagen type IV, murine laminin (both from Collaborative Research, Bedford, Mass.) and rat fibronectin (Chemicon Int., Temecula, Calif.). The antibodies used were polyclonal anti-rat collagen type I, anti-rat fibronectin and anti-mouse collagen type IV (Chemicon Int.), and anti-murine laminin (Collaborative Research). The polyclonal, rabbit anti-rat GLUT1 antibody used in the identification of GLUT1 was generated to specifically react with a 13 amino acid carboxy terminal peptide of this transporter isoform. The latter were obtained from East Acres Biologicals (Southbridge, Mass.). The affinity-purified, goat anti-rabbit IgG conjugated to 4 nm gold particles and the silver enhancement system IntenseSE™ used for the localization of GLUT1 at the light microscopic level, were obtained from Amersham Life Sciences Co. (Buckinghamshire, England). A monoclonal rabbit anti-rat Ig was used in the immunoblotting analysis of β-tubulin (Sigma Chemical Co., St. Louis Mo.).

The human GLUT1 gene (vector pSPGT) (Mueckler et al., 1985) was kindly provided by Dr. M. Mueckler (Dep. of Cell Biol. and Physiol., Washington Univ. School of Med., St. Louis Mo.). The fibroblast packaging cell line ΨCRE was kindly provided by Dr. R. Mulligan (Whitehead Inst. Biomed. Res., Mass. Inst. Technol., Cambridge, Mass.) and maintained in tissue culture as previously described (Freytag et al., 1994).

All MC tissue culture media were based on a special RPMI 1640 formulation lacking glucose, proline and glutamine (Gibco-93-5044EA, Gibco Laboratories, Grand Island, N.Y.) buffered with 25 mM Hepes. Proline L-[$^{14}$C (U)], 286 mCi/mmol; proline L-[2, 3, 4, 5, -$^3$H], 112 Ci/mmol; hydroxyproline L-4-[$^3$H (G)], 5.5 Ci/mmol; inulin [$^3$H (G)], 257 mCi/g; 2-deoxy[1-$^3$H]glucose, 30.6 Ci/mmol were all purchased from New England Nuclear Research Products (DuPont Co., Wilmington, Del.). The purity of the radioisotopic internal standards used in the quantitation of proline and hydroxyproline was established prior to their use by chromatographic analysis.

Additives to tissue culture media were cell culture-tested quality (Sigma Chemical Co). High purity Collagenase VII (Sigma Chemical Co.) was used in the protein-digestion assays. The bacterial myo-inositol dehydrogenase used in the measurement of myo-inositol was obtained from Sigma Chemical Co. The columns used for HPLC were 4.6 mm×25 cm Ultrasphere ODS, 5 μm particle size (Beckman Instruments Inc., San Ramon, Calif.).

Tissue Culture

MCs were obtained from Applicants' cloned line (16KC$_2$) derived from outgrowths of Fisher rat glomeruli and previously characterized by us (Dumler and Cortes, 1988). In brief, these cells demonstrate a fusiform or stellate appearance, intracellular fibrils, an ability to grow in medium containing D-valine, growth inhibition when cultured in the presence of heparin or mitomycin, a marked increase in guanosine 5'-cyclic monophosphate content upon exposure to atrial natriuretic peptide, and the presence of dense cytoplasmic immunochemical staining for collagen types I and IV, fibronectin, laminin and thrombospondin. In addition, these cells express the Thy-1 antigen and form "cell hillocks" containing dense extracellular matrix in post confluent cultures. These characteristics have been retained on repeated passage. Finally, applicants have recently shown that these cells demonstrate the same high sensitivity to phorbol-stimulated neutrophil adhesion and lysis (Varani et al., 1992) as do early passage MCs, indicating continued and like expression of essential cell surface receptors, including those for CD11/CD18 molecules.

Except where indicated, MCs were seeded (10,000 cells/cm$^2$) into 8 cm diameter plastic dishes or 2.5 cm diameter six-well plates (Corning Glass Works, Corning N.Y.) and grown in the medium described above to which penicillin, streptomycin, 20% Nu-Serum (Collaborative Research), 8 mM glucose, 2.05 mM glutamine, and an amount of proline to provide a final concentration of 183 μM (including proline contained in Nu-Serum), was added. Considering the high concentrations of glucose commonly occurring in a diabetic milieu (20–35 mM), a glucose concentration of 8 mM was considered as "normal". Lower concentrations of glucose were not used because MCs show deficient growth when maintained in the physiological concentration of 5 mM glucose (Ayo et al., 1990). Except for studies to determine growth rates, experiments were terminated seven days post seeding, when cultures had just reached confluency. Growth rates were determined in cells seeded in 8-well, 0.79 cm$^2$ glass chamber slides at a density of 12,600 cells/cm$^2$. Beginning on day 1, and on alternate days thereafter, cells were counted in four separate wells at each time period.

Preparation of Infective Virus and Transduction of Rat MCs

The procedures employed were similar to those previously reported (Freytag et al., 1994). Gene transductions were carried out using the pWZLneoMoMuLV retroviral vector (Ariad Co., Cambridge Mass.). This vector contains an internal ribosomal entry site from the encephalomyocarditis virus which allows for translation of the GLUT1 (GT1)and neomycin phosphotransferase (neo$^R$) gene products from the same RNA transcript. This property implies that cells acquiring resistance to the neomycin analog G418 will also express the GLUT1 gene product. Transcription of the discistronic proviral RNA is driven from the Moloney murine leukemia virus (MoMuLV) long terminal repeat.

The gene which encodes bacterial β-galactosidase (LacZ) or that encoding human GLUT1 (sense/antisense) was spliced into the multiple cloning site of pWZLneo. Once this was completed, pWZLneoLacZ and pWZLneoGT1 were used to transfect the ΨCRE fibroblast packaging cell line using a calcium phosphate precipitation method (Freytag and Geddes, 1992). After incubation of the transfected packaging cells for two days, the supernatants were removed, filtered through a 0.45 μm syringe filter and stored at −80° C. until used for transduction of MCs.

Normal MCs (16KC$_2$) in subconfluent cultures were transduced by exposure for two hours to the virus-containing supernatant in the presence of 8 μg/ml Polybrene (Sigma Immunochemicals). Cells were then washed and cultured for two days in the growth medium described above before their selection. Selection of stably transduced cells was carried out by two successive incubations, first, in a medium containing 0.25 mg/ml of the neomycin analog G418 (Sigma Immunochemicals) and then, in a medium in which the G418 concentration was doubled. A surviving clone exposed to pWZLneoLacZ was selected as a transduced MC control (MCLacZ) due to its high level of β-galactosidase expression according to the chromogenic dye X-gal (5-bromo-4-chloro-3-indolyl β-D-galactopyranoside) test (Bosh et al., 1993).

Surviving clone exposed to the vectors containing the GLUT1 gene (sense) are selected as a transduced MC overexpressing GLUT1 according to the levels of this product as determined by immunoblotting. Surviving clone exposed to the vectors containing the GLUT1 gene (antisense) are selected as a transduced MC underexpressing GLUT1 according to the levels of this product as determined by immunoblotting.

Northern Analyses

A standard method with slight modifications was used (Sharp et al., 1980). In brief, total RNA was obtained from cultures of MC using a commercially available kit based on the guanidinium and phenol extraction method (RNA Stat-60, Tel-Test Inc., Friendswood Tex.). RNA was denatured in glyoxal/DMSO and 20 μg samples loaded into individual lanes of a 1% agarose gel made with 10 mM sodium phosphate buffer. Electrophoretic separation was carried out in a circulating buffer gelbox (Hoeffer Super Sub, Hoeffer Scientific Instruments, San Francisco Calif.). Gels were then stained with ethidium bromide, destained and photographed. RNA integrity was confirmed by inspection of the ribosomal RNA bands. Gels were blotted to Genescreen membranes (Dupont NEN Research Products, Boston Mass.) and the RNA immobilized by UV irradiation. Blots were then prehybridized, and probed for the GLUT1 isoform, type I collagen, type IV collagen, fibronectin and the housekeeping gene β-tubulin using the respective cDNA's (1.66-kb human GLUT1, 1.5-kb proα1(I), 0.7-kb proα1(IV), 0.5-kb fibronectin). The latter were $^{32}$P-labeled by the Random Hexamer Priming method (PRIME-1 kit, Sigma Chemical Co.). Following exposure to Kodak XAR-5 film (Eastman Kodak, Rochester N.Y.) for 3–14 days, the autoradiograms were analyzed by optical scanning densitometry (Scan Master 3+, Howtek Inc., Hudson N.H.) using the NIH Image gel plotting software (NIH Image 1.52, Natl. Technical Information Service, Springfield Va.). Relative quantities of GLUT1 mRNA in cells were compared after normalization to mRNA for the housekeeping gene β-tubulin.

Immunoblotting of GLUT1

Immunoblot analysis was carried out according to methods previously described for the study of glucose transporter isoforms with minor modifications (Harrison et al., 1990). Fifty micrograms of solubilized protein samples were separated by SDS-PAGE and electrophoretically transferred to Hybond-ECL nitrocellulose membranes (Amersham, Arlington Heights, Ill.). As primary antibody, the rabbit anti-rat GLUT1 antibody described above was used. The secondary antibody was a horseradish peroxidase anti-rabbit-Ig conjugate (Amersham). Antigens were identified by a chemiluminescence assay based on the luminol reaction (ECL Western Blot kit, Amersham Life Sciences). Immunobloting of β-tubulin was used as a confirmatory method to assure the equal sample loading between gel lanes. Identification of GLUT1 bands was confirmed by preadsorption of anti-GLUT1 antiserum with 25 μg/ml of the purified GLUT1 peptide.

Measurement of Production of Extracellular Matrix Components; Enzyme-Linked Immunosorbent Assay In experiments in which specific extracellular matrix components were studied, production was quantified as the total amount accumulated in the tissue culture medium during 24 hours of incubation. At the start of this period, growth medium was changed to one in which Nu-Serum (Collaborative Biomedical) was replaced by 1% FCS. The presence of Nu-Serum or greater concentrations of FCS were found to result in increased backgrounds and reduced sensitivity of the ELISA. Removal of all serum during the collection period resulted in low recovery rates (3% or less) of added purified extracellular matrix components. Under the conditions used, recoveries were between 62 and 96% of added purified extracellular matrix components.

The amount of specific ECM components secreted into the culture medium was quantified by ELISA, using a modification of a procedure previously described (Riser et al., 1992). Samples of culture medium (50–100 μl) were added in triplicate to wells of a 96-well ELISA plate (Falcon, Bectin Dickinson Labware, Lincoln Park, N.J.) and incubated for 18 hours at 4° C. Purified matrix components, diluted in the same medium, were added (0.5 ng-1 μg/well) to each assay plate as standards. At the end of this incubation period, the medium was removed, and the unoccupied sites blocked by a 2-hour treatment with 5% non-fat dry milk (Carnation Co., Los Angeles, Calif.) in PBS containing 0.05% Tween. Wells were then washed and incubated for three hours with 100 μl of rabbit antisera for specific extracellular matrix components. All antisera were tested for specificity, before their use, by immunoblotting, with and without blocking, using the extracellular matrix standards described above. After extensive washing of the wells, an enzyme-linked alkaline phosphatase-labeled goat anti-rabbit IgG (Organon Teknika, Durham, N.C.) was added and the plates were incubated for an additional 3-hour period. This was followed by extensive washing and the addition of a phosphatase substrate solution (Sigma Chemical). Color intensity was measured with a Titertek Multiscan MCC/340 (Flow Laboratories, McLean, Va.), and results analyzed in a curve-fitter computer program (Interactive Microware Inc., State College, Pa.).

Study of Collagen Metabolism

Methods previously described (Riser et al., 1992) were used with modifications. The culture medium was changed 24 hours before the start of the radiolabeling period to a medium lacking proline (except for that contained in Nu-Serum which resulted in a final proline concentration of 40 μM). Preliminary experiments demonstrated no difference in growth rates between cells cultured in 40 μM or 0.174 mM proline over a 14-day period. Radiolabeling was carried out by incubation for 48 or 72 hours in an identical medium, but containing 0.15 mM β-aminopropionitrile, 210 μM ascorbic acid and 183 mM [$^{14}$C]-proline (82.3 mCi/mmole). Previous experiments by applicants demonstrated that [$^{14}$C]-proline incorporation into collagen increases linearly over a 72-hour period of radiolabeling (Riser et al., 1992). All tissue culture wells were supplemented every 24 hours to provide 140 μM fresh ascorbic acid. When the specific activity of the cellular proline endogenous pool was determined, 2.5 μCi of [$^3$H]-inulin/ml was added 15 minutes before the end of the radiolabeling period as an extracellular fluid marker, and the contents of each well thoroughly mixed. At the termination of the radiolabeling period, medium was rapidly aspirated, the plate placed on ice and 2–6 ml of cold 0.2 N perchloric acid poured onto the cell layer. The cell layer was not rinsed to remove residual medium, in order to avoid losses of intracellular free proline. In experiments done in 6-well plates, the media and cell layers of six wells were pooled as one sample for analysis.

Total protein contained in the medium samples was precipitated in 75% ethanol at −5° C., and the supernatant analyzed for [$^3$H]-inulin concentration. Following the addition of 89 μCi [$^3$H]-proline as internal standard, medium supernatants were filtered in Centricon™-3 filters (Amicon Co., Danvers, Mass.) and amino acids were separated by solid phase extraction using AG50W-X8 (H$^+$) columns (Poly-Prep®, Bio Rad Laboratories, Richmond, Calif.) and 6 N NH$_4$OH as eluant. After NH$_4$OH removal under vacuum (Speed-Vac concentrator, Savant Instruments Inc., Farmingdale, N.Y.), purified amino acids were resuspended in 0.1 N HCl for the subsequent determination of [$^{14}$C]-hydroxyproline, total proline, proline specific activity and calculation of the proline and [$^{14}$C]-proline/[$^3$H]-inulin ratios.

Net collagen accumulation in the medium was estimated by two independent methods. The first measurement was obtained according to the $^{14}$C incorporation into protein-associated hydroxyproline (Riser et al., 1992). In this method, the medium protein precipitate was hydrolyzed under vacuum with 6 N HCl at 110° C. for 18 hours and amino acids separated as above by solid phase extraction after the addition of 3.32 μCi [$^3$H]-hydroxyproline as an internal standard. These purified amino acids were subsequently analyzed for measurement of $^{14}$C incorporation into proline and hydroxyproline. The second method was based on the amount of total $^{14}$C incorporated into collagenase-digestible protein (Phan et al., 1985). In this method, following completion of the radiolabeling period, 1 ml of medium was mixed with 330 μl of a proteinase inhibitor solution (providing per milliliter: 3 μmole PMSF, 0.1 mmole EDTA, 40 μmole N-ethylmaleimide). Medium protein was precipitated and the pellet washed five times with cold 10% TCA. This precipitate was then resuspended in 1 N NaOH, incubated for 10 minutes at 37° C., and the solution neutralized with 1 N HCl. After adjusting the pH to 7.5 with 1 N tris buffer solution, PMSF and N-ethylmaleimide were added in the same amounts as before, and CaCl$_2$ added to provide a final 5 mM solution. For enzymatic digestion, the sample was divided into two equal portions and 140 units/ml of collagenase added to one of them, while the other was used as a control. After incubation for two hours at 37° C., the undigested protein was removed by precipitation with 10% TCA and 0.5% tannic acid. Finally, the $^{14}$C radioactivity in the supernatants and protein precipitate was measured and the radiolabel incorporation into collagenase-digestible and collagenase-resistant protein determined from the difference between the treated and non-treated samples.

Immediately after addition of 0.2 N perchloric acid, cell layers were scraped, briefly homogenized in the cold and the precipitates and acid-soluble supernatants separated by centrifugation. To measure the proline endogenous pool, these supernatants were neutralized at 4° C. with 1 N KOH to pH 7.0 and the concentration of [$^3$H]-inulin determined before the addition of 45 μCi of [$^3$H]-proline as an internal standard. The amino acids contained in this acid-soluble cell extract were separated by solid phase extraction as above, and lyophilized prior to measurement of cell layer-associated free [$^{14}$C]-hydroxyproline, free proline and proline specific activity. Because values for the ratios proline/[$^3$H]-inulin and [$^{14}$C]-proline/[$^3$H]-inulin in the medium from the same sample were known, the amount of proline and [$^{14}$C]-proline contributed by residual medium in the cell layer could be estimated in individual samples according to the amount of [$^3$H]-inulin measured in the cell layer acid extract, as done in previous studies (Riser et al., 1992). The cell layer's perchloric acid precipitate was lipid-extracted and consecutively subjected to alkaline and acid hydrolysis for the measurement of total RNA, DNA and the separation of protein (Munro and Fleck, 1966). The final protein precipitate was hydrolyzed as described above, [$^3$H]-hydroxyproline internal standard added, and amino acids purified and separated for the quantitation of $^{14}$C incorporation into proline and hydroxyproline.

Measurement of 2-Deoxyglucose Uptake Rates and Kinetics

The uptake of glucose was determined by using the nonmetabolizable analog 2-deoxy-D-[1-$^3$H]glucose according to a modification of the method of McClain et al. (1987). MCs were seeded in 35 mm diameter wells at a density of 42,000 cells/cm$^2$ and allowed to attach for two hours. After removal of the medium and rinsing with PBS, cultures were incubated in glucose-free PBS for 30 minutes and then, this buffer solution replaced with one containing 0.1 μCi/ml of the radiolabeled analog (3.27 nM). One milliliter of this solution was added per well and the samples were incubated for five minutes. Following this, the unincorporated radio-isotope was rapidly removed by washing the cell layer with cold PBS and cells were harvested for counting by trypsinization. In order to determine the kinetics of glucose uptake for the two different cell types, similar experiments to those described above were carried out using 13 different media concentrations of D-glucose between 0 and 24 mM. Results were expressed per milligram protein as determined in parallel culture plates. Lineweaver-Burk double reciprocal plots were used for the calculation $K_m$ and $V_{max}$.

Chromatography

Amino acids were analyzed as their precolumn-dansylated derivatives by reverse phase HPLC as previously described (Riser et al., 1992). In brief, derivatization was carried out at room temperature at pH 9.0 in a 3.5/1 molar ratio of 5-dimethylaminonaphthalene-1-sulfonyl (dansyl) chloride/amino acids for 20 hours. Analyses were performed using a Beckman 344 HPLC (Beckman Instruments) and 0.05 M monosodium phosphate/acetic acid buffer, pH 7.0, as the initial eluant and acetonitrile as the final eluant. Sample size was 46 and 355 nmole of amino acid residues for analysis of samples from supernatants and protein precipitates, respectively. A linear gradient between 10 and 25% acetonitrile at 1.5 ml/min flow rate resulted in optimal separation of hydroxyproline and proline in 46 minutes. The column effluent was monitored for fluorescence (Spectroflow 980 fluorescence detector, Applied Biosystems, Ramsey, N.J.) at 350 nm excitation and 470 nm emission wavelengths, and 0.3 ml fractions collected for measurement of $^3$H and $^{14}$C content. The recovery of the [$^3$H]-labeled proline and hydroxyproline was 43–77% and 70–96%, respectively.

All radioactivity measurements were carried out using Optiphase Hisave II (LKB Scintillation Products, Loughborough, England) as scintillator in a 3-channel liquid scintillation counter providing quench compensation (Beckman LS-3801, Beckman Instruments, Irvine Calif.).

Immunogold Labeling

The presence of cell-associated GLUT1 was studied by light microscopic examination of immunogold silver-stained samples of acetone-fixed MC cultures (Al-Nawab and Davies, 1993). Cells were seeded in 0.79 cm$^2$ wells at 12,600 cells/cm$^2$. At five days of growth the medium was aspirated and the cell layer washed with PBS followed by fixation in acetone for 10 minutes. After air-drying, the specimens were immersed in PBS for 20 minutes, placed in 1% BSA for one hour at room temperature and then incubated with the anti-GLUT1 antibody. Following extensive washing in PBS, the gold-conjugated secondary antibody was applied for two hours at 25° C. and the specimens washed again in PBS. Finally, samples were treated with glutaraldehyde and the labeling enhanced with the Amersham silver solution following the manufacturers instructions. Light microscopic examination was made in Mayer's hematoxylin counterstained specimens.

Chemical Measurements

Myo-Inositol was measured spectrophotometrically by following the reduction of NAD during the inositol dehydrogenase reaction (Weissbach, 1974). D-Sorbitol was analyzed by modification of a colorimetric method (Bergmeyer et al.) based on the sorbitol dehydrogenase reaction and the NADH-induced reduction of iodonitrotetrazolium chloride (Test-combination D-sorbitol/Xylitol, Boehringer Mannheim, Indianapolis, Ind.). Lactate was measured according to the NADH formed during the lactate dehydrogenase reaction utilizing a commercially available kit (Sigma Diagnostics Lactate, Sigma Chemical Co.). D-glucose was measured by a colorimetric method based on the glucose oxidase-peroxidase reaction (glucose procedure no. 510 kit, Sigma Diagnostics). Protein was measured by the method of Lowry using BSA as the standard.

RNA was measured by the orcinol reaction for quantitation of its ribose content. With this method 1 µg of yeast RNA (Type I, Sigma Chemical Co.) is equivalent to 0.6 µg of ribose (Cortes et al., 1982). DNA was measured by its ultraviolet absorption by a 2 wavelength ratio method (Tsaneve and Markov, 1960) using calf-thymus DNA (Type I, Sigma Chemical Co.) as reference standard. Total amino acids were quantified by a modified ninhydrin method (Doi et al., 1981) using L-leucine as the standard.

Expression of Results and Statistical Analyses

Depending on the type of experiment, results were expressed as per unit protein in the cell layer or as per cell or DNA, and presented as means±SEM. With the methods utilized, the cellular content of DNA was 27.4±1.74 pg. The optical density of the bands in the immunoblotting analyses was expressed in arbitrary units and the final results presented as percent change from control values.

The net collagen accumulation in the medium and in the cell layer was expressed according to the amount of [$^{14}$C]-proline incorporated into protein-associated [$^{14}$C]-hydroxyproline, while the incorporation into protein-associated [$^{14}$C]-proline was considered as an index of total protein synthesis. In the alternate method, net collagen accumulation in the medium was measured as the total $^{14}$C radioactivity incorporated into collagenase-digestible protein and total protein synthesis as the $^{14}$C radioactivity incorporated into collagenase-resistant protein. Collagen breakdown was estimated as the total newly formed free hydroxyproline, i. e., the sum of the medium and cell layer [$^{14}$C]-hydroxyproline detected as free amino acid. Total collagen synthesis was quantified as the total [$^{14}$C]-hydroxyproline formed, free or protein-associated, in the whole tissue culture sample. All results were adjusted for recovery rates of pure radiolabeled internal standards. Incorporation values were individually corrected in each sample for the specific activity of the medium free proline at the completion of the labeling period, and presented as nmol of proline incorporated per 24 hours of radiolabeling.

Differences between groups were evaluated using Student's t test for non-paired samples and the distribution of t in a 2-tailed test. Since previous studies demonstrated that collagen synthesis may be inversely related to tissue culture cell density in subconfluent cultures (Riser et al., 1992), significant differences in incorporation results were confirmed by analysis of covariance. In this analysis, to remove the effect of differences in cell content, the total amount of DNA in the sample was added as a regressor affecting the dependent variable (incorporation).

Example 1 Cell Lines Overexpressing GLUT1

Figure 8:
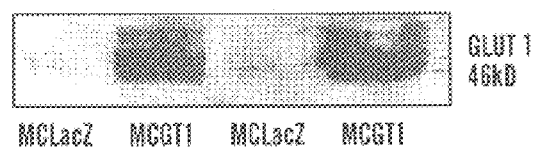
FIG. 8 is a photograph of an immunoblot of GLUT1 in MCLacZ and MCGT1 cells chronically adapted to 8 mM glucose RPMI 1640 medium, GLUT1 specific antibody was used to identify GLUT1 protein in the two cell types at 48 kD, duplicate immunoblot analyses of 50 μg protein samples, obtained from the cell layers of confluent cultures, are shown, GLUT1 protein is demonstrated in MCLacZ and MCGT1 cells as single bands of very different intensity migrating at 48 kD, Note that GLUT1 expression is markedly increased in the MCGT1 cells, approximately 10-fold higher than in MCLacZ cells, consistent with the immunogold-silver labeling seen in FIG. 6.

Summary: A full length human GLUT1 cDNA in the sense orientation was spliced into a commercial retroviral expression vector, pWZLneo (Ariad Co., Cambridge, Mass.) and is labeled as pWZLneoGLUT1S. This construct was transferred via the MoMuLV maloney murine leukemia virus vector to rat mesangial cells cultured in 8 mM glucose RPMI 1640 medium. G418-resistant clones (0.5 mg/ml) were screened by immunoblotting for overexpression of GLUT1. A mesangial cell clone was isolated (MCGT1) which overexpressed GLUT1 10-fold (FIG. 8).

Figure 9:
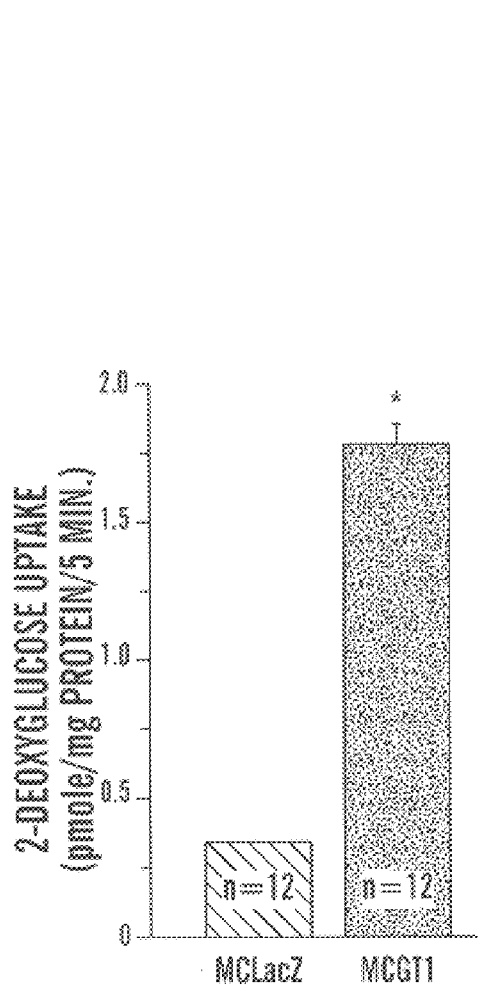
FIG. 9 is a bar graph of [$^3$H]2-deoxyglucose uptake rates in MCLacZ and MCGT1 cells, cells were grown to confluence in 8 mM glucose RPMI 1640 medium, then prepared for glucose uptake measurements using trace (3.27 pmol/ml) concentrations of [$^3$H]2-deoxyglucose (2-DOG), measurements were made at 5 minutes, on the linear portion of the glucose uptake curve, rates are expressed as pmol/mg protein/5 minutes, MCGT1 cells exhibited a substantially higher glucose uptake rate.
Figure 10:
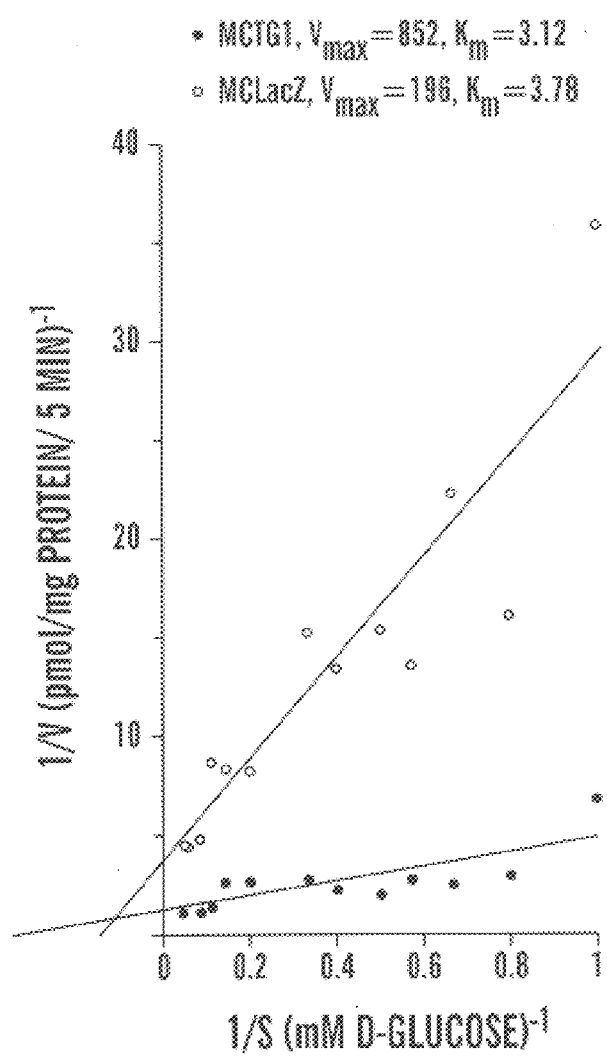
FIG. 10 is a Lineweaver-Burk plot of glucose uptake in MCLacZ and MCGT1 cells, cells were chronically adapted to 8 mM glucose medium, $V_{max}$ was 4.3× higher in MCGT1 cells, while $K_m$ was unchanged, as expected.
Figure 11:
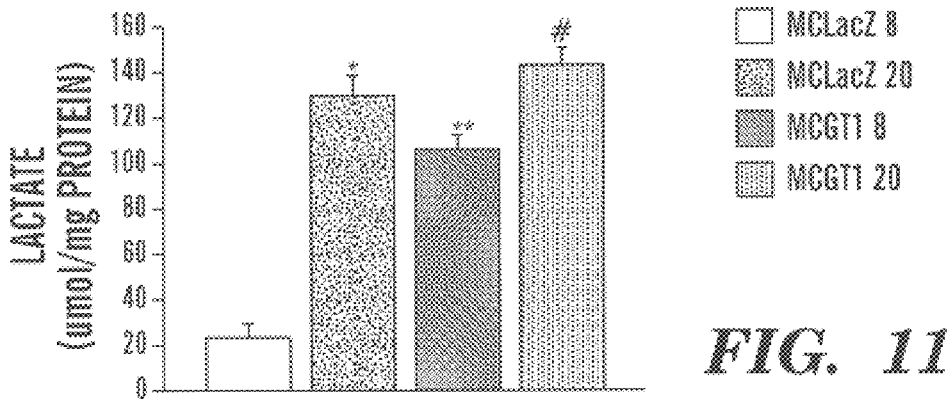
FIG. 11 is a bar graph of the lactate content of MCLacZ and MCGT1 cells, perchloric acid extracts were made from the two cell types, which had been chronically adapted to 8 mM glucose medium, cell lactate contents (umol/mg protein) were determined spectrophotometrically using a commercial test system (Sigma Co.) based on the LDH reaction.
Figure 12:
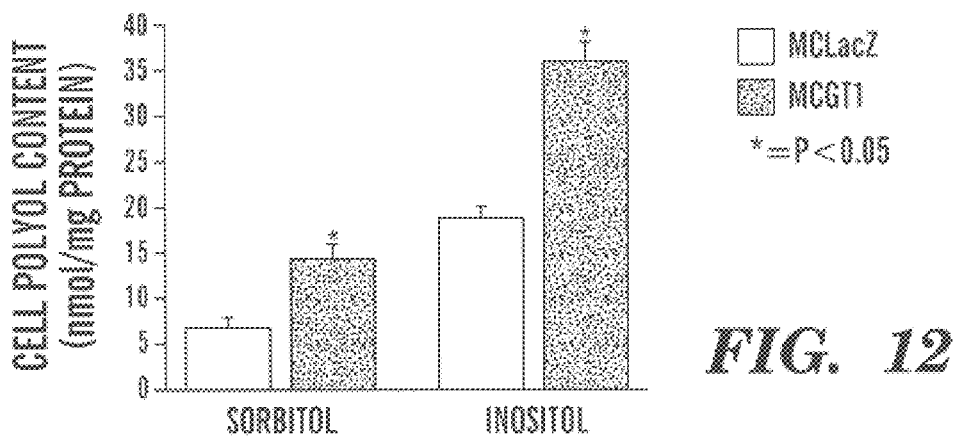
FIG. 12 is a bar graph of the polyol contents of MCLacZ and MCGT1 cells, perchloric acid extracts of the two cell types were prepared for measurements of sorbitol and myo-inositol (MI), both were measured using spectrophotometric assays based on NAD/NADH conversion, cells were chronically adapted to 8 mM glucose medium, both sorbitol and inositol contents were significantly higher in MCGT1 cells.
Figure 13A:
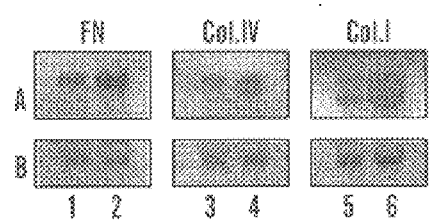
FIGS. 13A–B is (A) a comparison of Northern blots of ECM mRNAs (row A) in MCLacZ (lanes 1,3,5) and MCGT1 (lanes 2,4,6) cells, cells were grown to confluence in 8 mM glucose RPMI 1640 medium and total RNA was then harvested for both cell types, 20 μg total RNA was loaded to each lane of Na$_3$PO$_4$ gels for electrophoresis and Northern blots were probed for fibronectin (FN), type IV collagen (col.IV) and type I collagen (Col.I) using specific cDNA probes with each mRNA normalized to endogenous β-tubulin mRNA (row B), (B) Data were then converted to bar graph format for comparison, (*)=P<0.05)
Figure 13B:
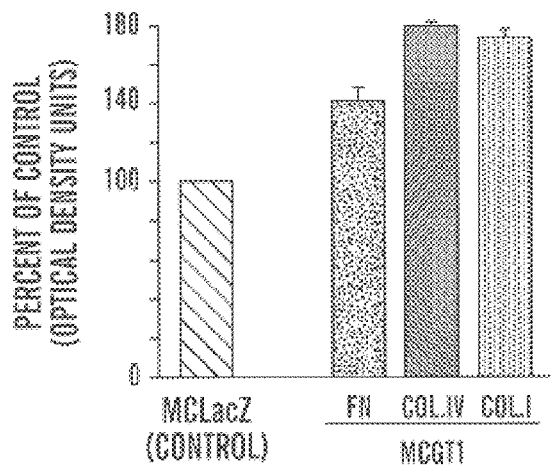
Figure 14:
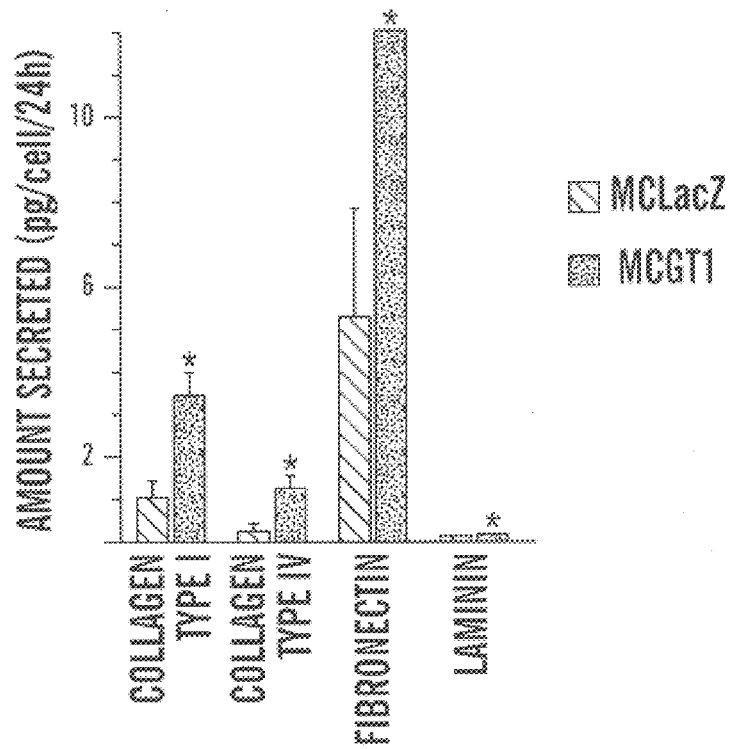
FIG. 14 is a bar graph showing ECM production in MCLacZ and MCGT1 cells, individual ECM( components released into the medium from cells were determined by use of ELISAs for FN, Col.IV, Col. I., and LN (laminin), production was assessed over 24 hour intervals, and expressed as pg/cell/24 hours (*)=P<0.05.

Glucose uptake rates were measured with [$^3$H]2-deoxyglucose (FIGS. 9, 10). Lactate, sorbitol, and inositol were all increased in MCGT1 cells in normal glucose medium (FIGS. 11, 12). ECM mRNAs (FN, type I collagen, type IV collagen) were all increased in MCGT1 cells in normal glucose medium (FIG. 13). Extracellular matrix (ECM) proteins secreted into the medium (Type I collagen (Col.1), TypeIV collagen (Col.IV), Fibronectin (FN) and laminin (LN) were quantitated by ELISA, and expressed as pg/cell/24 hrs (FIG. 14).

The glucose uptake rate was 450% higher in MCGT1 cells than in control MCLacZ cells which had been transduced with the reporter gene β-galactosidase (LacZ), (FIG. 9). Changes in ECM production are listed below:

| | ECM production (pg/cell/24 hrs) | | | |
|---|---|---|---|---|
| | Col.I | Col.IV | FN | LNMC |
| MCLacZ | 1.05 ± 0.33 | 0.29 ± 0.14 | 5.28 ± 2.54 | 0.09 ± 0.04 |
| MCGT1 | 3.38 ± 0.63 | 1.24 ± 0.28 | 12.0 ± 2.0 | 0.21 ± 0.03 |
| P value | <0.001 | <0.001 | <0.005 | <0.001 |

In more detail the following results were obtained:

Gene Construction and Characterization of LacZ and GLUT1 Expression Vectors

Construction of the pWZLneo expression vector is depicted in FIG. 5. The GLUT1 cDNA was first removed from the vector pSPGT by cutting with BamH1 and then spliced into the BamH1 cloning site of pWZLneo. Digestion with EcoR1 confirmed the 5'→3' orientation of the insert.

Expression of GLUT1 mRNA and GLUT1 Protein

The G418-resistant LacZ transduced MCs expressed large quantities of β-galactosidase as shown by the X-gal staining test. In addition these cells, grown in 8 mM glucose, expressed substantial amounts of GLUT1 mRNA (FIG. 7).

The level of GLUT1 mRNA increased 18-fold in MCGT1 cultured in the same conditions. MCLacZ also expressed the glucose transporter protein, as demonstrated by immunogold localization and immunoblot analysis (FIGS. 6, 8). As compared to these controls, MCGT1 cells cultured in the same glucose concentration demonstrated a 10-fold enhanced expression of GLUT1 protein that was evident in immunoblotting analyses (FIG. 8) and in immunogold studies (FIG. 6). The latter also demonstrated that this change was generalized and of a similar magnitude in all the MCGT1 cells. In addition, this overexpression was still present at similar levels after three months in cultures maintained in the same normal glucose concentration, as demonstrated by immunoblot analysis.

Glucose Transport and Kinetics

Preliminary experiments demonstrated that, under the conditions selected, 2-deoxyglucose uptake increased linearly with time over the first 10 minutes of incubation. As compared to the MCLacZ controls, the five minute uptake of the glucose analog in MCGT1 cells was markedly augmented (FIG. 9), suggesting a greatly enhanced entry of glucose in cells overexpressing GLUT1. In support of these findings, kinetic analyses revealed a 4.3-fold higher $V_{max}$ in MCGT1 vs. MCLacZ cells (P<0.001) (FIG. 10). In addition, the $K_m$ values for the rat (MCLacZ) and human (MCGT1) transporters were similar (P>0.2) and within the expected range of values (FIG. 10).

Cell Growth

Exposure of normal MCs to 35 mM glucose for seven days resulted in a moderately diminished proliferating activity and slight cell hypertrophy, as shown by a 17% significantly lower DNA content and an 8% significantly higher RNA/DNA ratio in cells cultured in high glucose concentration (Table I). Changes similar to these, but greatly exaggerated, were observed in MCGT1 cells cultured in normal glucose concentrations. At the end of the same observation period, cultures of MCGT1 cells demonstrated a 33% lower content of DNA and a 38% higher RNA/DNA ratio than their MCLacZ controls (Table I). The lower proliferative activity of the MCGT1 cultures as compared to MCLacZ cultures was also identified by analysis of growth curves obtained over a 15-day period of culture (not shown). Therefore, the inhibition of replication and hypertrophic effects associated with exposure of normal MCs to high extracellular glucose concentrations were also present under normal glucose concentration in cells with enhanced glucose transport, albeit these changes were greatly magnified.

Metabolic Characteristics

To determine if the enhanced glucose uptake induced by the overexpression of GLUT1 transporter was also associated with an increased metabolism of the hexose, lactate and sorbitol contents were measured as indices of substrate utilization. Under the same conditions of normal glucose concentration as above, lactate release into the medium as well as that associated with the cell layer were 2.5 and 2.2-fold greater, respectively, in MCGT1 cultures than in their MCLacZ counterparts (Table II). In similar experiments, cell sorbitol content was also increased 2.1-fold in MCGT1 cultures (Table II). Interestingly, this sorbitol accumulation was also associated with a significantly increased content of cell myo-inositol (Table II). These findings suggest that an increased glucose transport in MCs is linked to the greater metabolism of this sugar, at least via the glycolytic and polyol pathways.

Production of Extracellular Matrix Components

The secretion into the medium of specific extracellular matrix components was studied in MCGT1 cells to establish whether enhanced glucose transport, albeit in an environment of normal glucose concentration, could effectively stimulate the synthesis of the main components of mesangial matrix. As compared to their MCLacZ controls, MCGT1 cells secreted significantly more collagen type I, collagen type IV, fibronectin and laminin (FIG. 14).

Northern analyses for individual matrix components demonstrated fibronectin mRNA as a single band and collagens I and IV as their characteristic doublets (Haverty et al., 1992; Olsen et al., 1989). Differences in the secretion of extracellular matrix components likely resulted from increased synthesis in MCGT1 cells because their respective mRNAs were elevated 43 to 80% as compared with their MCLacZ controls (FIG. 13).

Collagen Metabolism in Conditions of High Glucose Concentration and High Glucose Transport Activity To analyze in detail how collagen metabolism may be altered by the presence of high glucose concentrations or by the enhanced glucose transport, the synthesis and catabolism of collagen was studied in normal MCs cultured in 8 or 35 mM glucose and in transduced MCs cultured in 8 mM glucose. The incorporation rate of radiolabeled amino acid precursor into protein is strongly influenced by changes in the specific activity of its endogenous pool. Therefore, initial experiments were done to evaluate the effect of medium glucose concentration on medium and endogenous pool proline specific activity. At the completion of the incubation period, medium proline specific activity was 88% and 94% of the initial value in media containing 8 and 35 mM glucose, respectively. The difference between these two groups was significant (8 mM, 133,717±6,068, n=6; 35 mM, 149,000±3,810 dpm/nmol proline, n=6, P<0.0001). These changes in medium proline specific activity were mirrored by those occurring in the cellular endogenous pool of proline. Thus, at the end of the incubation period proline endogenous pool specific activity was also significantly lower in samples incubated in 8 mM glucose (8 mM, 87,468±5,389, n=6; 35 mM, 102,650±7,516 dpm/nmol proline, n=6, P=0.0004). Since calculation of incorporation results according to the specific activity of proline in the endogenous pool or in the incubation media did not alter the differences between groups, all results were expressed according to the final specific activity of free proline in the sample's incubation medium.

In normal MCs, exposure to 35 mM glucose for a period of 12 days induced a 69% increase in collagen synthesis (Table III). This change was associated with an 80–90% greater net accumulation of newly formed collagen in the medium, as measured by two independent radiolabeling methods. There was an inverse relationship between the amount of DNA in the sample and collagen accumulation (P=0.0005). When the effect of different DNA content was removed by analysis of covariance, the differences between groups were still significant (P=0.0001). In addition, the accumulation of collagen in the cell layer (much lower than into the medium due to the presence of β-aminopropionitrile) was also increased by 68%. The increment in collagen synthesis caused by glucose was also associated with a 59% greater catabolism. Although the fraction of the collagen produced undergoing catabolism was significantly lower in high glucose concentration cultures, comparison of the magnitude of the changes in synthesis and catabolism reveal that the main cause for net collagen accumulation was enhanced formation.

The increase in collagen accumulation in the incubation medium coincided with a stimulation in overall protein secretion as measured by the two radiolabeling methods (Table III) (collagenase-resistant protein: 8 mM, 42.6±1.4, n=8; 35 mM, 79.5±3.9 nmole proline/mg DNA/24 hours, n=8, P<0.0001). However, the change in collagen formation was significantly greater than that for total protein (Table III).

At the completion of the labeling period, medium proline specific activity did not differ in the two groups of transduced cells cultured in 8 mM glucose (MCLacZ, 205,288±3,030, n=6; MCGT1, 200,230±3,290, n=6). MCGT1 cells demonstrated a 109% increase in total collagen synthesis, associated with a 111–117% greater net accumulation, as compared to their MCLacZ controls (Table IV). As in experiments in normal mesangial cells, there was a significant effect of the sample's DNA content on the collagen accumulated (P=0.005). After this effect was eliminated in an analysis of covariance, the differences between groups were still significant (P=0.015). This augmented collagen accumulation in the medium was part of an overall enhancement in protein synthesis as suggested by results from the two methods used in this study (Table IV) (collagenase-resistant protein: MCLacZ, 45.6±13.3, n=6; MCGT1, 82.8±10.7 nmole proline/mg DNA/24 hours, n=6, P=0.055). Nevertheless, as shown above in normal cells, the synthesis of collagen was particularly stimulated in MCGT1 cells (Table IV). The amount of collagen accumulated in the cell layer was also increased in MCGT1 cells by 64% of the value for MCLacZ cells. Also, as shown in normal MCs, the greater collagen synthesis in MCGT1 cells was associated with a marked increase in collagen catabolism. However, the fraction of collagen produced which was catabolized was similar in both types of cells, therefore, the net collagen accumulation demonstrated in medium and cell layer of MCGT1 cultures was fully attributable to an increased rate of synthesis.

Medium was regularly changed at 48-hour intervals during the period of cell growth. Subsequently, during the 3-day proline radiolabeling period, without replenishment of the medium, the MCGT1 cells demonstrated a 42-fold greater net glucose utilization (Table IV), which caused a decrease in the medium glucose concentration from 8 mM to values approximating 5 mM.

From the above data, it can be concluded that:

1) Rat MCs transduced with the pWZLneoGLUT1S DNA expression construct (MCGT1 cells) markedly overexpress the functional transporter.

2) MCGT1 exhibits up to 4-fold increased production of ECM without any exposure to increased extracellular glucose concentrations.

3) Therefore, changes in glucose transport alone can stimulate pathways which are pathologic in diabetes.

TABLE I

Growth of normal control rat mesangial cells (MC) and transduced rat mesangial cells overexpressing human GLUT1 protein (MCGT1) or bacterial β-galactosidase protein (MCLacZ).*

|  | DNA ($\mu$g) | RNA ($\mu$g)/DNA (mg) |
|---|---|---|
| MC 8 mM Glucose | 96.29 ± 5.17 | 136.3 ± 2.22 |
| MC 35 mM Glucose | 84.00 ± 1.67‡ | 146.8 ± 3.5§ |
| MCLacZ 8 mM Glucose | 91.32 ± 1.57 | 151.8 ± 2.7 |
| MCGT1 8 mM Glucose | 60.87 ± 1.72∥ | 210.2 ± 1.7∥ |

*Results were obtained in cultures at 7 days of growth. To compare the relative effects of 35 mM glucose and GLUT1 overexpression, experiments demonstrating similar DNA in the MC control and MCLacZ groups were selected. Values are mean ± SEM of 6 samples in each group.
‡$P$ = 0.047, §$P$ = 0.031, significant from MC, 8 mM Glucose.
∥$P$ < 0.0001, significant from MCLacZ.

TABLE II

Metabolic characteristics of transduced rat mesangial cells overexpressing human GLUT1 protein (MCGT1) or bacterial β-galactosidase protein (MCLacZ) grown in the presence of normal glucose concentrations.*

|  | MCLacZ (n = 4) | MCGT1 (n = 4) |
|---|---|---|
| Lactate Production (mmole/mg protein/72h) |  |  |
| Medium | 4.16 ± 0.57 | 10.58 ± 0.85 |
| Cell | 1.66 ± 0.10 | 3.66 ± 0.21§ |
| Cellular Sorbitol Content (nmole/mg protein) | 6.54 ± 1.26 | 14.07 ± 1.33‡ |
| Cellular *Myo*-inositol Content (nmole/mg protein) | 18.4 ± 1.41 | 35.65 ± 2.02§ |

*Results were obtained in cultures grown to confluency in 8 mM glucose. Values are mean ± SEM.
‡$P$ < 0.005, §$P$ < 0.0001

TABLE III

Collagen metabolism in rat mesangial cells exposed to high glucose concentrations.*

|  | 8 mM Glucose (n = 8) | 35 mM Glucose (n = 8) |
|---|---|---|
| Total Collagen Synthesis (nmole Pro incorporated into total Hyp) | 69.10 ± 1.58 | 117.11 ± 2.76‡ |
| Medium Collagen Accumulation (nmole Pro incorporated into protein-associated Hyp) | 32.28 ± 0.65 | 58.33 ± 1.58‡ |
| Medium Collagen Accumulation (nmole Pro incorporated into collagenase-sensitive protein) | 46.94 ± 0.79 | 89.37 ± 2.78‡ |
| Medium Total Protein Accumulation (nmole Pro incorporated into protein) | 166.6 ± 10.5 | 250.8 ± 11.2‡ |
| Medium Fractional Collagen Accumulation (collagen formation as percent of total protein) | 16.47 ± 0.66 | 18.96 ± 0.39§ |
| Cell layer Collagen Accumulation (nmole proline incorporated into protein-associated Hyp) | 0.766 ± 0.046 | 1.286 ± 0.09∥ |
| Total Collagen Catabolism (nmole proline incorporated into free Hyp) | 36.05 ± 1.14 | 57.49 ± 1.40‡ |
| Fractional Collagen Catabolism (percent of total collagen catabolized) | 52.11 ± 0.63 | 9.10 ± 0.46¶ |

*Results were obtained after 48 h of incubation with 183 $\mu$M radiolabeled proline. Incorporation data were corrected for the media specific radioactivity of the precursor and expressed per milligram of DNA/24th. Values are mean ± SEM. Pro, proline; Hyp, 4-hydroxyproline.
‡$P$ < 0.0001, §$P$ = 0.0056, ∥$P$ = 0.0002, ¶$P$ = 0.0017

TABLE IV

Collagen metabolism and glucose utilization in transduced rat mesangial cells overexpressing human GLUT1 protein (MCGT1) or bacterial β-galactosidase protein (MCLacZ) exposed to normal glucose concentrations.*

|  | MCLacZ (n = 6) | MCGT1 (n = 6) |
|---|---|---|
| Total Collagen Synthesis (nmole Pro incorporated into total Hyp) | 102.33 ± 1.66 | 214.37 ± 4.49‡ |
| Medium Collagen Accumulation (nmole Pro incorporated into protein-associated Hyp) | 23.37 ± 0.41 | 49.35 ± 2.04‡ |

TABLE IV-continued

Collagen metabolism and glucose utilization in transduced rat mesangial cells overexpressing human GLUT1 protein (MCGT1) or bacterial β-galactosidase protein (MCLacZ) exposed to normal glucose concentrations.*

|  | MCLacZ (n = 6) | MCGT1 (n = 6) |
|---|---|---|
| Medium Collagen Accumulation (nmole Pro incorporated into collagenase-sensitive protein) | 39.66 ± 2.94 | 86.06 ± 6.01‡ |
| Medium Total Protein Accumulation (nmole Pro incorporated into protein) | 131.71 ± 5.54 | 238.16 ± 8.69‡ |
| Medium Fractional Collagen Accumulation (collagen formation as percent of total protein) | 15.14 ± 0.43 | 17.16 ± 0.20§ |
| Cell layer Collagen Accumulation (nmole proline incorporated into protein-associated Hyp) | 1.419 ± 0.046 | 2.323 ± 0.113‡ |
| Total Collagen Catabolism (nmole proline incorporated into free Hyp) | 77.53 ± 1.32 | 162.70 ± 3.12‡ |
| Fractional Collagen Catabolism (percent of total collagen catabolized) | 75.73 ± 0.25 | 75.92 ± 0.58 |
| Net Glucose Utilization (μmole) | 2.69 ± 6.51 | 116.20 ± 5.98‡ |

*Results were obtained after 72_h of incubation with 183_μM radiolabeled proline. Incorporation data were corrected for the media specific radioactivity of the precursor and expressed per milligram of DNA/24th. Values are mean ± SEM. Pro, proline; Hyp, 4-hydroxyproline.
‡P < 0.0001, §P = 0.0018

Example 2 Cell Lines Underexpressing GLUT1

The MCGT1AS cell clone has been transduced with the pWZLneoGLUT1AS DNA expression construct. The latter DNA construct is stably integrated in the genome of the mesangial cells where it constitutively produces a near full length antisense GLUT1 mRNA attached to additional RNA sequence coded by the expression vector. This polycistronic mRNA molecule is referred to in FIG. 16 as "Proviral RNA," and is approximately 5.6 kb in size. Because it contains antisense GLUT1 RNA sequence it is recognized by a GLUT1 cDNA probe as shown in FIG. 16.

Figure 16:
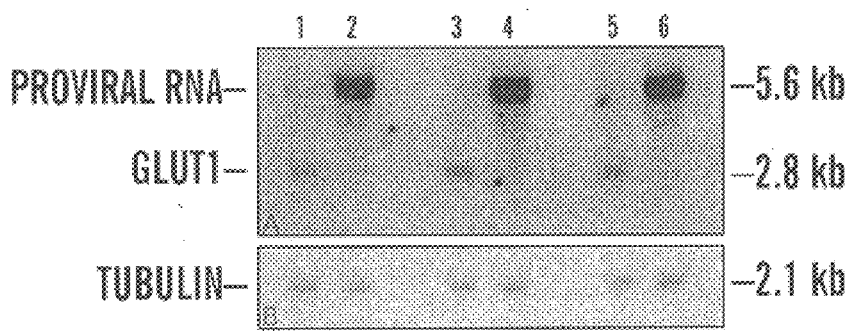
FIG. 16 is a photograph of a Northern blot of GLUT1 mRNA (sense and antisense) in MCLacZ and MCGT1 cells using a double-stranded GLUT1 cDNA probe for GLUT1, RNA samples for MCLacZ vs MCGT1AS cells were run in triplicate, endogenous (sense) GLUT1 mRNA in MCLacZ control cells at 2.8 Kb is seen in lanes 1, 3 and 5 and its near disappearance in MCGT1AS (antisense GLUT1 treated) cells in lanes in 2, 4 and 6 due to transduction of the cells with the antisense GLUT1 construct which produces a new 5.6 Kb mRNA shown in lanes 2, 4, 6, which binds-up the endogenous sense GLUT1 mRNA, leading to its inactivation and degradation, therefore, less endogenous (sense) GLUT1 mRNA is available for making GLUT1 protein.

The antisense GLUT1 RNA produced from the integrated DNA construct is complementary to the cells' endogenous (sense) GLUT1 mRNA strand which is shown at 2.8 kb in FIG. 16. This complementarity allows the two strands to bind to each other, with the duplex presumably being degraded by RNAses. Consequently, the endogenous (sense) GLUT1 mRNA level is diminished in the antisense GLUT1 treated cells as shown in lanes 2, 4 and 6 of FIG. 16 which represent RNA from MCGT1AS (antisense treated) cells. The antisense GLUT1 RNA band at 5.6 kb remains bright because there is a large excess of the RNA molecule in the cells: the ratio of antisense GLUT1 RNA to sense GLUT1 RNA in the cells was determined to be greater than 6 to 1. This ratio was adequate to reduce the sense GLUT1 mRNA to approximately 50% of its normal level.

Figure 17:
FIG. 17 is a photograph of an immunoblot of GLUT1 in MCLacZ and MCGT1AS cells, cells were grown to confluence in 8 mM glucose RPMI 1640 medium and total proteins were isolated for each cell type, 50 μg loaded to each lane of a 10% SDS-PAGE gel for electrophoresis, electroblots were then probed with GLUT1-specific antibody to identify GLUT1 protein at 48 kD, GLUT1 is significantly decreased in the MCGT1AS cells, consistent with the decrease in GLUT1 mRNA, lanes 1 and 3 show GLUT1 in MCLacZ control cells, lanes 2 and 4 show GLUT1 in MCGT1AS cells.
Figure 18:
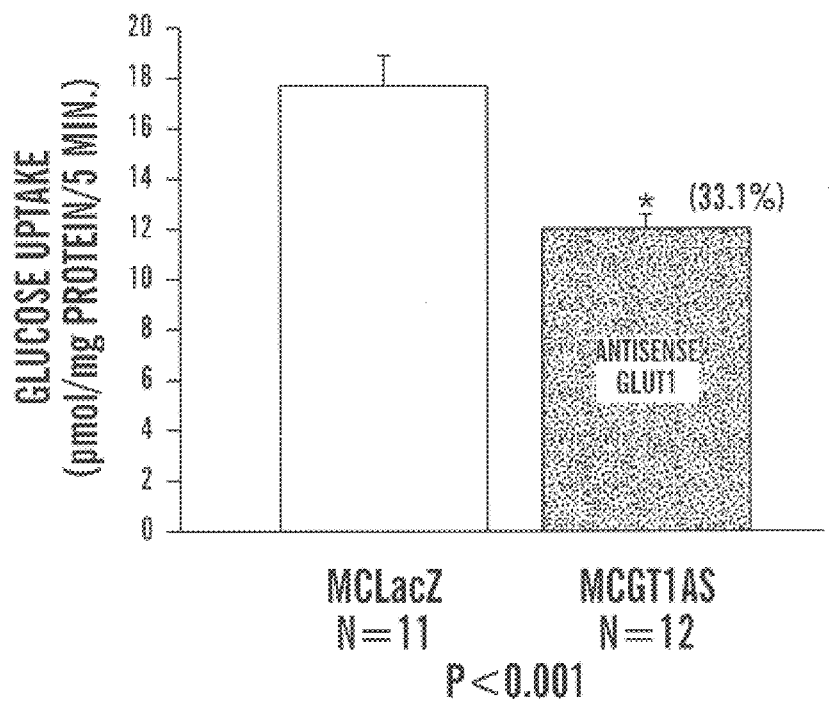
FIG. 18 is a graph of $^3$H2-deoxyglucose uptake rates in MCLacZ and MCGT1AS cells, cells were grown to confluence in 8 mM glucose RPMI 1640 medium and were then harvested for measurements of glucose uptake by exposure to trace (3.27 pmol/ml) concentrations of [$^3$H]2-deoxyglucose (2-DOG) for 5 minutes, on the linear portion of the glucose uptake curve, glucose uptakes are expressed as pmol/mg protein/5 minutes.

Corresponding with the diminished GLUTA1 mRNA in MCGT1AS cells was an approximate 50% decrease in GLUT1 protein (FIG. 17, lanes 2 and 4), and a 33.1% decrease in glucose uptake rate (FIG. 18). The combination of the results of these Northern analyses, Western analyses, and [³H]2-deoxyglucose uptake rate measurements, indicated the antisense GLUT1 treatment had substantially suppressed GLUT1 expression and glucose transport in the MCGT1AS clone of mesangial cells.

Subsequently, applicants tested the ability of antisense GLUT1 treatment to protect mesangial cells from the adverse effects of high glucose by subjecting the cells to high glucose concentrations in the diabetic range (20 mM glucose=360 mg/dl) and measuring FN (ECM) gene expression. The MCLacZ and MCGT1AS cells have been adapted to standard 8 mM glucose (140 mg/dl) and maintained therein. Subsequently they were passed, grown in 8 mM glucose medium for 3 days, then switched to 20 mM high glucose medium for 2 weeks. Normally, mesangial cells respond to high extracellular glucose by increasing FN mRNA, and consequently FN protein.

Total RNA was collected from the MCLacZ and MCGT1AS cells which had been exposed to 20 mM glucose for 2 weeks, and Northern analyses were used to determine the relative amounts of FN mRNA. Applications found that FN mRNA was reduced 52% compared with its level in MCLacZ cells (FIG. 19, FN mRNA at 7.9 Kb). This indicated that antisense GLUT1 therapy of mesangial cells was effective in suppressing FN (ECM) gene expression in response to high glucose, with the implication that antisense GLUT1 therapy may be able to protect kidney mesangial cells and glomeruli in vivo from the hyperglycemia of diabetes, which otherwise would induce scarring of the glomeruli by inducing excessive ECM (eg. FN or scar tissue) production.

The pWZLneoGLUT1AS construct described in this application can be used to transduce proliferating mesangial cells on other cell types, either in vitro or in vivo. Human, mouse or rat cells can be transduced with this construct as it is carried by an amphotropic MoMuLV vector. There is, therefore, therapeutic potential for the pwzlneoGLUT1AS construct which codes for antisense GLUT1 RNA and consequently the suppression of cellular GLUT1 expression and glucose uptake.

Throughout this application various publications are referenced. Full citations for the publications not provided hereinabove are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCEs

Abboud, "Platelet-derived growth factor and mesangial cells" Kidney Int. 41:581–583 (1992).

Abboud et al., "Production of platelet-derived growth factorlike protein by rat mesangial cells in culture" J. Clin. Invest. 80:675–683 (1987).

Al-Nawab and Davies "Demonstration of extracellular immunoglobulin in renal tissues with silver enhanced colloidal gold" J. Histotechnol. 16:235–242 (1993).

Ayo et al., "High glucose causes an increase in extracellular matrix proteins in cultured mesangial cells" Am. J. Pathol. 136:1339–1348 (1990).

Ayo et al., "Increased extracellular matrix synthesis and mRNA in mesangial cells grown in high glucose medium" Am. J. Physiol. 260 (Renal Fluid and Electrolyte Physiol. 29):F185–191 (1991a).

Ayo et al., "High glucose increases diacylglycerol mass and activates protein kinase C in mesangial cell cultures" Am.

J. Physiol. 261 (Renal Fluid Electrolyte Physiol. 30):F571–F577 (1991b).

Baldwin, "Mammalian passive glucose transporters: Members of a ubiquitous family of active and passive transport proteins" Biochem. Biophys. Acta 1154:17–49 (1993).

Barbosa et al., "Effect of glycemic control on early diabetic renal lesions. A 5-year randomized controlled clinical trial of insulin-dependent diabetic kidney transplant recipients" J. Am. Med. Assoc. 272:600–606 (1994).

Bergmeyer et al., "D-Sorbitol assay" In Methods of Enzymatic Analysis H. U. Bergmeyer editor. Academic, New York. 1323–1326.

Bilous et al., "Mean glomerular volume and rate of development of diabetic nephropathy" Diabetes 38:1142–1147 (1989a).

Bilous et al., "The effects of pancreas transplantation on the glomerular structure of renal allografts in patients with insulin-dependent diabetes" New Engl. J. Med. 321:80–85 (1989b).

Bosh et al., "Gene transfer into the mammalian kidney: direct retrovirus transduction of regenerating tubular epithelial cells" Exp. Nephrol. 1:49–54 (1993).

Brosius et al. "Insulin-responsive glucose transporter expression in renal microvessels and glomeruli" Kidney Int. 42:1086–1092 (1994).

Chatzilias and Whiteside, "Cellular mechanisms of glucose-induced myo-inositol transport upregulation in rat mesangial cells" Am. J. Physiol. 267 (Renal Fluid Electrolyte Physiol. 36):F459–F466 (1994).

Choi et al., "Rat mesangial cell hypertrophy in response to transforming growth factor-$\beta 1$" Kidney Int. 44:948–b 958 (1993).

Concepcion et al., "D-glucose stimulates mesangial cell (MC) GLUT1 expression, glucose uptake, and IGF1-induced glucose transport" Abstract submitted to ASN, (1995a).

Concepcion et al., "Identification of mesangial cell (MC) PKC isoforms, activation states and extracellular matrix (ECM) gene expression in MC overexpressing GLUT1" Abstract submitted to ASN (1995b).

Concepcion et al., "Development of a new in vitro model for protection of the mesangial cell (MC) against diabetes: retroviral-mediated antisense inhibition of GLUT1" Abstract submitted to ASN (1995c).

Cortes et al., "Effects of early diabetes on uridine diphosphosugar synthesis in the rat renal cortex" Kidney Int. 21:676–682 (1982).

Craven and Derubertis, "Protein kinase C is activated in glomeruli from streptozotocin diabetic rats. Possible mediation by glucose" J. Clin. Invest. 83:1667–1675 (1989).

Danne et al., "Effect of high glucose on type IV collagen production by cultured glomerular epithelial, endothelial, and mesangial cells" Diabetes 42:170–177 (1993).

Diabetes Control and Complication Trial Research Group. "The effect of intensive treatment of diabetes on the development and progression of long-term complications in insulin-dependent diabetes mellitus" The Diabetes Control and Complications Trial Research Group. New England Journal of Medicine 329(14):977–86 (Sep. 30, 1993).

Doi et al., "Modified colorimetric ninhydrin method for peptidase assay" Anal. Biochem. 118:173–184 (1981).

Dumler and Cortes, "Uracil ribonucleotide metabolism in rat and human glomerular epithelial and mesangial cells" Am. J. Physiol. 255 (Cell Physiol. 24):C712–C718 (1988).

Floege et al., "Infusion of platelet-derived growth factor or basic fibroblast growth factor induces selective glomerular mesangial cell proliferation and matrix accumulation in rats" J. Clin. Invest. 92:2952–2962 (1993).

Freytag et al., "Ectopic expression of the CCAAT/enhancer-binding protein promotes the adipogenic program in a variety of mouse fibroblastic cells" Genes & Dev. 8:1654–1663 (1994)

Freytag and Geddes, "Reciprocal regulation of adipogenesis by Myc and C/EBP$\alpha$" Science 256:379–382 (1992).

Fumo et al., "PKC and high glucose stimulate collagen $\alpha_1$ (IV) transcriptional activity in a reporter mesangial cell line" Am. J. Physiol. 267 (Renal Fluid Electrolyte Physiol. 36):F632–F638 (1994).

Gilbert et al., "Long-term glycemic control and the rate of progression of early diabetic kidney disease" Kidney Int. 44:855–859 (1993)

Gilboa, et al., Transfer and expression of cloned genes using retroviral vectors. BioTechniques 4(6):504–512, 1986.

Gould and Holman, "The glucose transporter family: structure, function and tissue specific expression" Biochem. J. 295:329–341 (1993).

Guzman and Crews, "Regulation of inositol transport by glucose and protein kinase C in mesangial cells" Kidney Int. 42:33–40 (1992).

Haneda et al., "Glucose enhances type IV collagen production in cultured rat glomerular mesangial cells" Diabetologia 34:198–200 (1991)

Harrison et al., "Suppressed intrinsic catalytic activity of GLUT1 glucose transporters in insulin-sensitive 3T3-L1 adipocytes" Proc. Natl. Acad. Sci. USA 88:7839–7843 (1991).

Harrison et al., "Insulin regulation of hexose transport in mouse 3T3-L1 cells expressing the human HepG2 glucose transporter" J. Biol. Chem. 265:20106–20116 (1990).

Haverty et al., "Tubular antigen-binding proteins repress transcription of type IV collagen in the autoimmune target epithelium of experimental interstitial nephritis" J. Clin. Invest. 89:517–523 (1992).

Heilig et al., "Overexpression of glucose transporters in rat mesangial cells cultured in a normal glucose milieu mimics the diabetic phenotype" In press, J. Clinical Investigation (1995a).

Heilig et al., "Immunogold localization of high affinity GLUT isoforms in normal rat kidney" In press, Laboratory Investigation (1995b).

Heilig et al., "Overexpression of GLUT1 in rat mesangial cells (MC): a new model to simulate diabetes" JASN 5(3):965 (1994).

Heilig et al., "Identification of facilitative glucose transporters (GT) in mesangial cells (MC)" J. Am. Soc. Nephrol. 3:758. (Abstract)(1992).

Hiraki et al., "Growth factors rapidly induce expression of the glucose transporter gene" J. Biol. Chem. 263:13655–13662 (1988).

Hundal et al., "Cellular mechanism of metformin action involves glucose transporter translocation from an intracellular pool to the plasma membrane in L6 muscle cells" Endocrinology 131:1165–1173 (1992).

Imai et al., "Introduction of a foreign gene into the kidney in vivo: development of glomerulosclerosis by the transfection of genes for PDGF and TGF-beta. Contributions to Nephrology 107:205–15 (1994).

Inman and Colowick, "Stimulation of glucose uptake by transforming growth factor $\beta$: Evidence for the requirement of epidermal growth factor-receptor activation" Proc. Natl. Acad. Sci. USA 82:1346–1349 (1985).

Isaka et al., "Glomerulosclerosis induced by in vivo transfection of transforming growth factor-β or platelet-derived growth factor gene into the rat kidney" *J. Clin. Invest.* 92:2597–2601 (1993).

Kahn, "Facilitative glucose transporters: Regulatory mechanisms and dysregulation in diabetes" *J. Clin. Invest.* 89:1367–1374 (1992).

Kaiser et al., Differential regulation of glucose transport and transporters by glucose in vascular endothelial and smooth muscle cells" *Diabetes* 42:80–89 (1993).

Kaname et al., "Autocrine secretion of transforming growth factor-β in cultured rat mesangial cells" *Kidney Int.* 42:1319–1327 (1992).

Kikkawa et al., "Glut1 is a main glucose transporter in rat mesangial cells" *J. Am. Soc. Nephrol.* 3:830. (Abstract) (1992).

Kitagawa et al., "Regulation of glucose transport activity and expression of glucose transporter mRNA by serum, growth factors and phorbol ester in quiescent mouse fibroblasts" *Biochem. Biophys. Acta* 980:100–108 (1989).

Kitamura et al., "Gene transfer into the rat renal glomerlus via a mesangial cell vector: site-specific delivery, in situ amplication, and sustained expression of an exogenous gene in vivo" *J. Clinical Investigation* 94(2):497–505 (1994).

Kreisberg et al., "High glucose elevates c-fos and c-jun transcripts and proteins in mesangial cell cultures" *Kidney Int.* 46:105–112 (1994).

Kreisberg and Ayo, "The glomerular mesangium in diabetes mellitus" *Kidney Int.* 43:109–113 (1993).

Kreisberg, "Hyperglycemia and microangiopathy. Direct regulation by glucose of microvascular cells" *Lab. Invest.* 67:416–426 (1992).

Klip et al., "Regulation of expression of glucose transporters by glucose: a review of studies in vivo and in cell cultures" *FASEB J.* 8:43–53 (1994).

Ladson-Wofford et al., "High extracellular glucose concentrations increase receptors for transforming growth factor-β (TGFβ) in rat mesangial cells (MC) in culture" *J. Am. Soc. Nephrol.* 5:696. (Abstract)

Larkin and Dunlop, "The link between hyperglycemia and diabetic nephropathy" *Diabetologia* 35:499–504 (1992).

Loike et al., "Hypoxia induces glucose transporter expression in endothelial cells" *Am. J. Physiol.* 236 (Cell Physiol. 32):C326–C333 (1992).

Okuda et al., "Elevated expression of transforming growth factor β and proteoglycan production in experimental glomerulonephritis. Possible role in expansion of the mesangial extracellular matrix" *J. Clin. Invest.* 86:453–462 (1990).

Marette et al., "Abundance, localization, and insulin-induced translocation of glucose transporters in red and white muscle" *Am. J. Physiol.* 263 (Cell Physiol. 32):C443–C452 (1992).

Mauer et al., "Structural-functional relationships in diabetic nephropathy" *J. Clin. Invest.* 74:1143–1155 (1984).

McClain et al., *J. Biol. Chem.* 262:14663–14671 (1987).

Merrall et al., "Insulin and platelet-derived growth factor acutely stimulate glucose transport in 3T3-L1 fibroblasts independently of protein kinase C" *Biochem. Biophys. Acta* 1177:191–198 (1993).

Moran et al., "Effects of IGF-1 and glucose on protein and proteoglycan synthesis by human fetal mesangial cells in culture" *Diabetes* 42:170–177 (1991).

Mueckler et al., "Sequence and structure of a human glucose transporter" *Science* 229:941–945 (1985).

Munro and Fleck, "The determination of nucleic acids" *Methods Biochem. Anal.* 12:113–176 (1966).

Nahman et al., "Effects of high glucose on cellular proliferation and fibronectin production by cultured human mesangial cells" *Kidney Int.* 41:396–402 (1992).

Olsen et al., "Collagen gene expression by cultured human skin fibroblasts" *J Clin Invest* 83:791–795 (1989).

Petersen et al. "Effect of insulin therapy on established diabetic nephropathy in rats" *Diabetes* 37:1346–1350 (1988).

Phan et al., "Rat lung fibroblast collagen metabolism in bleomycin-induced pulmonary fibrosis" *J. Clin. Invest.* 76:241–247 (1985).

Rash, "Prevention of diabetic glomerulopathy in streptozotocin diabetic rats by insulin treatment. The mesangial regions" *Diabetologia* 17:243–248 (1979).

Riser et al., "Intraglomerular pressure and mesangial stretching stimulate extracellular matrix formation in the rat" *J. Clin. Invest.* 90:1932–1943 (1992).

Riser et al., "Interactive effect of high glucose and stretch on mesangial cell (MC) collagen (COL) metabolism: role of TGF-β." *Annual Meeting American Society of Nephology*, (submitted, 1995).

Rollins et al. "Platelet-derived growth factor regulates glucose transporter expression" *J. Biol. Chem.* 236:16523–16526 (1988).

Sarabia et al., "Glucose transport in human skeletal muscle cells in culture. Stimulation by insulin and metformin" *J. Clin. Invest.* 90:1386–1395 (1992).

Scheinman et al. "Collagen synthesis by human glomerular cells in culture" *Biochem. Biophys. Acta* 542:128–136 (1978).

Seyer-Hansen et al., "Renal hypertrophy in experimental diabetes. A morphometric study" *Diabetologia* 18:501–505 (1980).

Sharp et al., "Transcription maps of adenovirus" *Meth. Enzymol.* 65:750–768 (1980).

Shetty et al., "Induction of GLUT1 mRNA in response to inhibition of oxidative phosphorylation" *Am. J. Physiol.* 265 (Cell Physiol. 34):C1224–C1229 (1993).

Sivitz et al., "Regulation of glucose transporter messenger mRNA in insulin-deficient states" *Nature* 340:72–74 (1989).

Smardo et al., "Kidney aldose reductase gene transcription is osmotically regulated" *Am. J. Physiol.* 263:C776–82 (1992).

Steffes et al., "Amelioration of mesangial volume and surface alterations following islet transplantation in diabetic rats" *Diabetes* 29:509–515 (1980).

Steffes et al., "Cell and matrix components of the glomerular mesangium in type I diabetes" *Diabetes* 41:679–684 (1992).

Studer et al., "Role for protein kinase C in the mediation of increased fibronectin accumulation by mesangial cells grown in high-glucose medium" *Diabetes* 42:118–126 (1993).

Thorens et al., "Molecular physiology of glucose transporters" *Diabetes Care* 13:209–218 (1990).

Tordjman et al., "Differential regulation of two distinct glucose transporters species expressed in 3T3-L1 adipocytes: Effect of chronic insulin and tolbutamide treatment" *Proc. Natl. Acad. Sci. USA* 86:7761–7765 (1989).

Tsanev and Markov, "Substances interfering with spectrophotometric estimation of nucleic acids and their elimination by the two-wavelength method" *Biochim. Biophys. Acta* 42:442–452 (1960).

Varani et al., "Mesangial cell killing by leukocytes: Role of leukocyte oxidants and proteolytic enzymes" *Kidney Int.* 42: 1169–1177 (1992).

Wang et al., "Coordinate regulation of glucose transporter function, number, and gene expression by insulin and sulfonylureas in L6 rat skeletal muscle cells" *J. Clin. Invest.* 84:62–67 (1989).

Weissbach, "myo-Inositol assay" In *Methods of Enzymatic Analysis* H. U. Bergmeyer editor. Academic, New York. 1333–1336 (1974).

Wolf et al., "High glucose-induced proliferation in mesangial cells is reversed by autocrine TGFβ" *Kidney Int.* 42:647–656 (1992).

Yaoita et al., "Isolation and characterization of proteoglycans synthesized by cultured mesangial cells" *J. Biol. Chem.* 265:522–531 (1990).

Ziyadeh et al., "Stimulation of collagen gene expression and protein synthesis in murine mesangial cells by high glucose is mediated by autocrine activation of transforming growth factor-β" *J. Clin. Invest.* 93:536–542 (1994).

What is claimed is:

1. An isolated mesangial cell which is transduced with a DNA molecule encoding the GLUT1 a glucose transporter protein so that said isolated transduced mesangial cell overexpresses the glucose transporter compared to untransduced mesangial cells and exhibits a diabetic phenotype.

2. An isolated mesangial cell according to claim 1, wherein said isolated transduced mesangial cell produces, compared to untransduced mesangial cells, two to four times more extracellular matrix, at least two times more sorbitol, and at least 2.5 times more lactants, all in standard 8 mM glucose medium.

3. An isolated mesangial cell according to claim 1, wherein said cell is MCGT1.

4. A method of screening compounds suitable for treatment of diabetic nephropathy comprising:

providing a first screening mixture comprising:
an isolated mesangial cell which is transduced with a DNA molecule encoding the GLUT1 a glucose transporter protein so that said isolated transduced mesangial cell overexpresses the glucose transporter compared to untransduced mesangial cells and exhibits a diabetic phenotype and
a candidate compound;

monitoring the effect of the candidate compound on production of extracellular matrix by the isolated transduced mesangial cell in the first screening mixture; and identifying, as a potential therapeutic for treatment of diabetic nephropathy, the candidate compound in any first screening mixture where production of extracellular matrix is reduced.

5. A method according to claim 4, wherein said isolated transduced mesangial cell in the first screening mixture is transduced with a vector containing the DNA molecule encoding the glucose transporter, said method further comprising:

providing a second screening mixture comprising:
an isolated mesangial cell transduced with the vector used to transduce the isolated mesangial cell of the first screening mixture but lacking the DNA molecule encoding the glucose transporter and
a candidate compound, wherein said monitoring further comprises monitoring the effect of the candidate compound on production of extracellular matrix by the isolated mesangial cell in the second screening mixture and said identifying further comprises identifying the candidate compound where production of extracellular matrix in the first screening mixture is at a level which is reduced partially or completely to the level of extracellular matrix production in the second screening mixture.

6. A method according to claim 5, wherein the mesangial cell in the second screening mixture is MCLacZ.

7. A method according to claim 5, wherein the mesangial cell in the first screening mixture is MCGT1.

8. A method according to claim 5, wherein said isolated mesangial cell in the first screening mixture produces, compared to the isolated mesangial cell of the second screening mixture, two to four times more extracellular matrix, at least two times more sorbitol, and at least 2.5 times more lactants, all in standard 8 mM glucose medium.

9. A DNA expression system designated pWZLneo-GLUT1.

* * * * *